US011649430B2

(12) United States Patent
Keller

(10) Patent No.: US 11,649,430 B2
(45) Date of Patent: May 16, 2023

(54) METHOD TO INDUCE SPORE GERMINATION IN FUNGI

(71) Applicant: Wisconsin Alumni Research Foundation, Madison, WI (US)

(72) Inventor: Nancy P. Keller, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 852 days.

(21) Appl. No.: 16/550,720

(22) Filed: Aug. 26, 2019

(65) Prior Publication Data

US 2020/0063092 A1 Feb. 27, 2020

Related U.S. Application Data

(60) Provisional application No. 62/723,058, filed on Aug. 27, 2018.

(51) Int. Cl.

| | |
|---|---|
| ***C12N 1/38*** | (2006.01) |
| ***A01N 43/90*** | (2006.01) |
| ***C12N 1/14*** | (2006.01) |

(52) U.S. Cl.

CPC ............... *C12N 1/38* (2013.01); *A01N 43/90* (2013.01); *C12N 1/14* (2013.01)

(58) Field of Classification Search

CPC ............. C12N 1/38; C12N 1/14; A01N 43/90

See application file for complete search history.

(56) References Cited

PUBLICATIONS

Saima Khalid, Joshua A. Baccile, Joseph E. Spraker, Joanna Tannous, Muhammad Imran, Frank C. Schroeder, and Nancy P. Keller, NRPS-Derived Isoquinolines and Lipopetides Mediate Antagonism between Plant Pathogenic Fungi and Bacteria, 2018, ACS Chem. Biol., vol. 13, pp. 171-179, published Nov. 28, 2017 (Year: 2017).*

Arrebola, et al., (2010) Iturin A is the principal inhibitor in the biocontrol activity of Bacillus amyloliquefaciens PPCB004 against postharvest fungal pathogens. *J. Appl. Microbiol. 108*, 386-395.

Averyanov et al. (1990) Activated Oxygen as a Possible Factor in the Autoinhibition of Spore Germination of the Fungus Pyricularia-Oryzae. *Biochemistry-Moscow 55*, 1397-1402.

Averyanov et al. (2007) Suppression of early stages of fungus development by hydrogen peroxide at low concentrations. *Plant Pathol. J. 6*, 242-247.

Averyanov et al., (2011) Self-inhibition of spore germination via reactive oxygen in the fungus Cladosporium cucumerinum, causal agent of cucurbit scab. *Eur. J. Plant Pathol. 130*, 541-550.

Ayerst, G. (1969) The effects of moisture and temperature on growth and spore germination in some fungi. *J. Stored Prod. Res. 5*, 127-141.

Baccile et al., (2016) Plant-like biosynthesis of isoquinoline alkaloids in Aspergillus fumigatus. *Nat. Chem. Biol. 12*,419-424.

(Continued)

*Primary Examiner* — David W Berke-Schlessel

*Assistant Examiner* — Trent R Clarke

(74) *Attorney, Agent, or Firm* — Joseph T. Leone; DeWitt LLP

(57) ABSTRACT

A method of promoting fungal spore germination. The method includes the step of contacting a fungal spore with a germination-promoting concentration of an exogenous imizoquin.

25 Claims, 12 Drawing Sheets

(56) References Cited

PUBLICATIONS

Barkal LJ, Walsh NM, Botts MR, Beebe DJ, Hull CM. 2016. Leveraging a high resolution microfluidic assay reveals insights into pathogenic fun- gal spore germination. Integr Biol 8:603-615. https://doi.org/10.1039/ c6ib00012f.

Baskaran et al., (2016) Neferine prevents NF-κB translocation and protects muscle cells from oxidative stress and apoptosis induced by hypoxia. *Biofactors 42*, 407-417.

Bok et al., (2014) Illumina identification of RsrA, a conserved C2H2 transcription factor coordinating the NapA mediated oxidative stress signaling pathway in Aspergillus. *BMC Genomics 15*, 1011.

Botts et al., Isolation and characterization of Cryptococcus neoformans spores reveal a critical role for capsule biosynthesis genes in spore biogenesis. Eukaryotic Cell. Apr. 2009; 8(4):595-605. doi: 10.1128/ Ec.00352-08.

Chi et al., (2016) RacA-Mediated ROS Signaling is Required for Polarized Cell Differentiation in Conidiogenesis of Aspergillus fumigatus. *PLoS ONE 11*, e0149548.

Choi, Y. H. (2016) Berberine Hydrochloride Protects C2C12 Myoblast Cells Against Oxidative Stress-Induced Damage via Induction of Nrf-2-Mediated HO-1 Expression. *Drug Dev. Res. 77*, 310-318.

Dijksterhuis, J., Heat-resistant ascospores, Food Mycology: A Multifaceted Approach to Fungi and Food, Chapter 6, 101-117.

Dong et al., (2015) Increased Oxidative Stress in Cultured 3T3-L1 Cells was Attenuated by Berberine Treatment. *Nat. Prod. Commun. 10*, 895-897.

Fischer et al., (2017) Lipoxygenase Activity Accelerates Programmed Spore Germination in Aspergillus fumigatus. *Front. Microbiol. 8*, 831.

Hayward, A. C., (1991) Biology and epidemiology of bacterial wilt caused by pseudomonas solanacearum. *Annu. Rev. Phytopathol. 29*, 65-87.

Imamura et al., (2011) Identification and characterization of a novel fermented substance produced by edible Aspergillus oryzae AO-1 that inhibits DPP-IV activity. *J. Biosci. Bioeng. 111*, 37-40.

Imamura et al., (2012) Identification of a Gene Involved in the Synthesis of a Dipeptidyl Peptidase IV Inhibitor in Aspergillus oryzae. *Appl. Environ. Microbiol. 78*, 6996-7002.

Khaldi et al., (2010) SMURF: Genomic mapping of fungal secondary metabolite clusters . *Fungal Genet. Biol. 47*, 736-741.

Kong et al., (2014) The inhibitory effect of Bacillus megaterium on aflatoxin and cyclopiazonic acid biosynthetic pathway gene expression in Aspergillus flavus. *Appl Microbiol. Biotechnol. 98*, 5161-5172.

Liu et al., (2015) Biocontrol Activity of Bacillus subtilis Isolated from Agaricus bisporus Mushroom Compost Against Pathogenic Fungi. *J. Agric. Food Chem. 63*, 6009-6018.

Miyamoto et al., (2014) Formation of 1-octen-3-ol from Aspergillus flavus conidia is accelerated after disruption of cells independently of Ppo oxygenases, and is not a main cause of inhibition of germination. *PeerJ 2*, e395.

Murai et al., (2017) Ralstonins A and B, Lipopeptides with Chlamydospore-Inducing and Phytotoxic Activities from the Plant Pathogen Ralstonia solanacearum. *Org. Lett. 19*, 4175-4178.

Netzker et al., (2015) Microbial communication leading to the activation of silent fungal secondary metabolite gene clusters. *Front. Microbiol. 6*, 299.

Oh et al., (2010) Proteomic analysis of early phase of conidia germination in Aspergillusnidulans. *Fungal Genet. Biol. 47*, 246-253.

Olmedo et al., (2017) Antifungal activity of β-carbolines on Penicillium digitatum and Botrytis cinerea. *Food Microbiol. 62*, 9-14.

Porquier et al., (2016) The botrydial biosynthetic gene cluster of Botrytis cinerea displays a bipartite genomic structure and is positively regulated by the putative Zn(II)2Cys6 transcription factor BcBot6. *Fungal Genet. Biol. 96*, 33-46.

Qin et al., (2011) Biodiversity, bioactive natural products and biotechnological potential of plant-associated endophytic actinobacteria. *Appl. Microbiol. Biotechnol. 89*, 457-473.

Sato et al., (2009) Yhe glutathione system of Aspergillus nidulans involves a fungus-specific glutathione S-transferase. *J.Biol. Chem. 284*, 8042-8053.

Schrey et al., (2012) Production of fungal and bacterial growth modulating secondary metabolites is widespread among mycorrhiza-associated streptomycetes. *BMC Microbiol. 12*, 164.

Shimizu et al., (2001) Genetic involvement of a cAMP-dependent protein kinase in a G protein signaling pathway regulating morphological and chemical transitions in Aspergillus nidulans. *Genetics 157*, 591-600.

Spraker et al., (2016) Ralstonia solanacearum lipopeptide induces chlamydospore development in fungi and facilitates bacterial entry into fungal tissues. *ISME J 10*, 2317-2330.

Tarkka et al., (2009) Inter-kingdom encounters: recent advances in molecular bacterium-fungus interactions. *Curr. Genet. 55*, 233-243.

Tournas V. Heat-resistant fungi of importance to the food and beverage industry, *Crit Rev Microbiol*. 1994;20(4):243-63.

Tranquillini et al., (Feb. 2, 2017) Occurrence and ecological distribution of Heat Resistant Moulds Spores (HRMS) in raw materials used by food industry and thermal characterization of two Talaromyces isolates, *Int J Food Microbiol*., 242:116-123. doi: 10.1016/j. ijfoodmicro.2016.11.023. Epub Nov. 25, 2016.

Walsh, C. T. (2008) the chemical versatility of natural-product assembly lines. *Acc. Chem. Res. 41*, 4-10.

Walsh NM, Wuthrich M, Wang H, Klein B, and Hull CM. 2017. Characterization of C-type lectins reveals an unexpectedly limited interaction between *Cryptococcus neoformans spores* and Dectin-1. *PloS One* 12(3):0173866.

Yao et al., (2016) a cytoplasmic Cu—Zn superoxide dismutase SOD1 contributes to hyphal growth and virulence of Fusarium graminearum. *Fungal Genet. Biol. 91*, 32-42.

Zhao et al., (2014) Heat-induced oxidative injury contributes to inhibition of Botrytis cinerea spore germination and growth. *World J. Microbiol. Biotechnol. 30*, 951-957.

Zheng et al., (2015) Redox metabolites signal polymicrobial biofilm development via the NapA oxidative stress cascade in Aspergillus. *Curr. Biol. 25*, 29-37.

* cited by examiner c

COSY:
HMBC:

Imizoquin A, 1: R = H
Imizoquin B, 2: R = OH

Imizoquin C, 3

Imizoquin D, 4

TMC-2A (Wyk-1), 5: R = OH
TMC-2B, 6: R = H

Imizoquin A, 1: R = H
Imizoquin B, 2: R = OH
Imizoquin E, 7
TMC-2A (Wyk-1), 5: R = OH
TMC-2B, 6: R = H

METHOD TO INDUCE SPORE GERMINATION IN FUNGI

CROSS-REFERENCE TO RELATED APPLICATIONS

Priority is hereby claimed to provisional application Ser. No. 62/723,058, filed Aug. 27, 2018, which is incorporated herein by reference.

FEDERAL FUNDING STATEMENT

This invention was made with government support under GM112739 awarded by the National Institutes of Health. The government has certain rights in the invention.

BACKGROUND

Soil-associated microbial populations represent complex and dynamic microbiomes that communicate primarily through chemical signaling. Several recent studies demonstrated the importance of specialized metabolites derived from biosynthetic gene clusters (BGCs), including non-ribosomal peptide synthetase-based (NRPS), polyketide synthase-based (PKS), and terpene synthase-based clusters, in mediating specific interactions between bacteria and fungi.[1,2] Expression of most of these BGCs is strongly regulated by specific growth conditions or confrontations with other organisms. In fact, some otherwise silent BGCs are activated during interkingdom-encounters[3] whereas other are repressed during such encounters.[4]

Agricultural environments may include plant pathogens otherwise not found in the rhizosphere. In addition to many soil dwelling fungal pathogens, the wilt bacteria *Ralstonia solanacearum* infects a multitude of crops and persists in the soil through unclear mechanisms, potentially by colonizing weeds that remain asymptomatic.[5] It was recently found that *R. solanacearum* produces a genus of hybrid PKS-NRPS-derived lipopeptides called ralstonins (originally called ralsolamycin) that induce chlamydospore formation across disparate taxa of fungi. This facilitates bacterial entry into chlamydospore tissue which may benefit bacterial survival.[6] The structures of the ralstonins were recently characterized in detail by Mural et al.[7] It is not clear, however, whether chlamydospore development provides a competitive advantage to the colonized fungus. Although thick-walled chlamydospores can weather harsh environmental conditions, bacterial proliferation inside these spores may decrease survival of the fungus. We therefore hypothesized that ralstonin production, while conferring a fitness benefit to *Ralstonia*, may elicit a defensive response from challenged fungi, or, conversely ralstonin may act to suppress mechanisms favoring fungal over bacterial success.

Here we characterize antagonistic crosstalk mediated by ralstonin and a newly discovered class of fungal isoquinoline alkaloids, the imizoquins, where each compound retards some aspect of the growth dynamics of the other microbe. Imizoquins stimulate germination of *Aspergillus* spores whereas ralstonin production by *R. solanacearum* impedes spore germination of *A. flavus* and reduces expression of the imizoquin BGC. Conversely, imizoquins have a slight but significant effect on slowing *R. solanacearum* growth. Mechanistically, imizoquins possess ROS quenching properties that yield protective properties to fungal spores and exhibit conserved germination promoting properties across diverse *Aspergillus* spp. We propose that reciprocal antagonistic signaling molecules, as uncovered in this work, are likely representative of interactions in the microbial rhizosphere.

Isoquinoline is a heterocyclic aromatic organic compound. It is the 2-position structural isomer of quinoline.

Both isoquinoline and quinoline are benzopyridines, that is, a benzene ring fused to a pyridine ring. In quinolone, the nitrogen heteroatom of the fused pyridine ring is in the 1-position; in isoquinoline, the nitrogen heteroatom of the fused pyridine ring is in the 2-position:

Isoquinoline

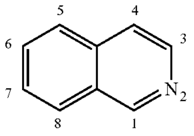

A number of isoquinoline derivatives are widely sold as pharmaceutical agents, such as dimethisoquin (an anesthetic), the ACE-inhibitor antihypertension drug quinapril, and the vasodilator papaverine.

SUMMARY

Bacterial-fungal interactions are presumed to be mediated chiefly by small-molecule signals. However, little is known about the signaling networks that regulate antagonistic relationships between pathogens. Ralstonins, lipopeptides produced by the plant pathogenic bacteria *Ralstonia solanacearum*, are shown herein to interfere with germination of the plant-pathogenic fungus *Aspergillus flavus* by down-regulating expression of a cryptic biosynthetic gene cluster named imq. Comparative metabolomic analysis of overexpression strains of the transcription factor ImqK revealed imq-dependent production of a family of tripeptide-derived alkaloids which have been given the name imizoquins. These alkaloids are produced via a non-ribosomal peptide synthetase-(NRPS)-derived tripeptide and contain an unprecedented tricyclic imidazo[2,1-a]isoquinoline ring system. We show that the imizoquins serve a protective role against oxidative stress that is essential for normal *A. flavus* germination. Supplementation of purified imizoquins restored wildtype germination to a □imqK *A. flavus* strain and protected the fungus from ROS damage. Whereas the bacterial ralstonins retarded *A. flavus* germination and suppressed expression of the imq cluster, the fungal imizoquins in turn suppressed growth of *R. solanacearum*. We suggest such reciprocal small molecule-mediated antagonism is a common feature in microbial encounters affecting pathogenicity and survival of the involved species.

Disclosed herein is the discovery of an antagonistic crosstalk mediated by ralstonins and a newly discovered class of fungal isoquinoline alkaloids, the imizoquins, wherein each class of compound retards some aspect of the growth dynamics of the other microbe. Imizoquins stimulate germination of fungal spores whereas ralstonin production by *R. solanacearum* impedes fungal spore germination and reduces expression of the imizoquin BGC. Conversely, imizoquins have a slight but significant effect on slowing *R. solanacearum* growth. This antagonism is illustrated schematically in FIG. 1. On the left side of the figure, the action imizoquins, whose production in the fungus *A. flavus* is driven by the imq biosynthetic gene cluster, is opposed by the ralstonins, shown on the right side of the figure. In the *R. solanacearum* bacterium, the production of the ralstonins is driven by the rmy biosynthetic gene cluster. Mechanistically, imizoquins possess reactive oxygen species (ROS)-quenching properties that yield protective properties to fungal spores and exhibit conserved fungal germination-promoting properties, notably across diverse *Aspergillus* species. The reciprocal antagonistic signaling molecules disclosed herein are likely representative of other uncharacterized interactions in the microbial rhizosphere.

Thus, disclosed herein is a method of promoting fungal spore germination. The method comprises contacting a fungal spore with a germination-promoting concentration of an exogenous imizoquin.

A second version of the method comprises contacting a fungal spore with a germination-promoting amount of an exogenous imizoquin having a structure as shown in Formula (I):

(I)

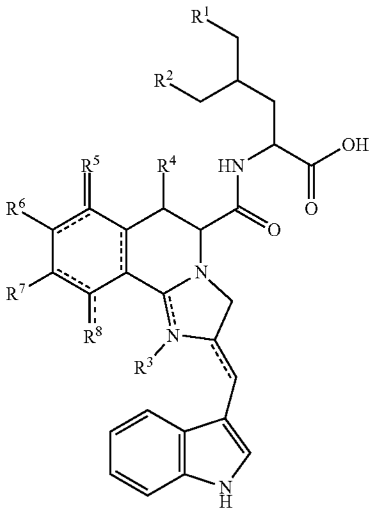

wherein $R^1$, $R^2$, $R^4$, and $R^6$ are independently selected from hydrogen or hydroxyl (—OH); $R^3$ is hydrogen or is absent; $R^5$ and $R^8$ are independently selected from hydrogen, hydroxyl, or oxo (=O); and $R^7$ is $C_1$-$C_6$-alkoxy; and salts thereof.

A third version of the method comprises contacting a fungal spore with a germination-promoting amount of an exogenous imizoquin having a structure as shown in Formula (I):

(I)

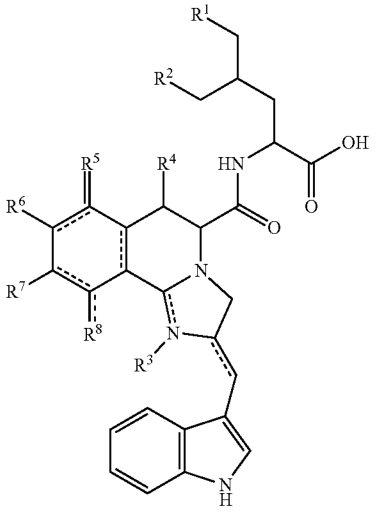

wherein $R^1$, $R^2$, and $R^6$ are independently selected from hydrogen or hydroxyl (—OH); $R^4$ is hydrogen; $R^3$ is hydrogen or is absent; $R^5$ and $R^8$ are oxo (=O); and $R^7$ is $C_1$-$C_6$-alkoxy; and salts thereof.

A fourth version of the method comprises contacting a fungal spore with a germination-promoting amount of an exogenous imizoquin having a structure as shown in Formula (I):

(I)

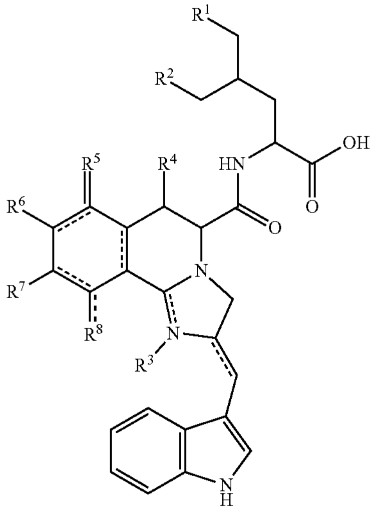

wherein $R^1$, $R^2$, and $R^6$ are independently selected from hydrogen or hydroxyl (—OH); $R^4$ is hydrogen; $R^3$ is hydrogen or is absent; $R^5$ and $R^8$ are hydroxy; and $R^7$ is $C_1$-$C_6$-alkoxy; and salts thereof.

A fifth version of the method comprises contacting a fungal spore with a germination-promoting amount of an exogenous imizoquin having a structure as shown in Formula (I):

(I)

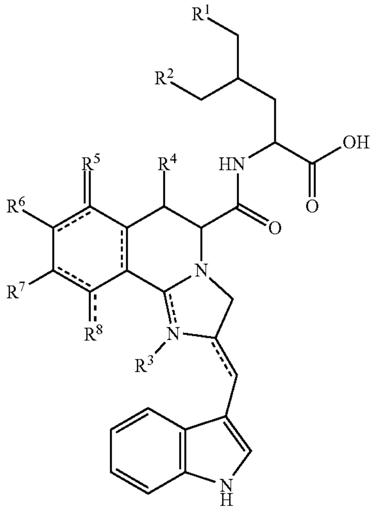

wherein $R^1$, $R^2$, and $R^6$ are independently selected from hydrogen or hydroxyl (—OH); $R^4$ is hydrogen; $R^3$ is hydrogen or is absent; $R^5$ and $R^8$ are oxo (=O); and $R^7$ is methoxy; and salts thereof.

A six version of the comprises contacting a fungal spore with a germination-promoting amount of an exogenous imizoquin having a structure as shown in Formula (I):

(I)

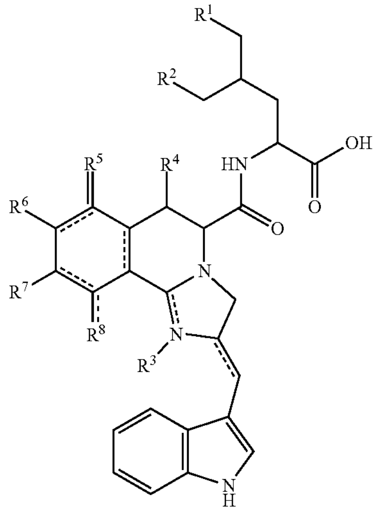

wherein $R^1$, $R^2$, and $R^6$ are independently selected from hydrogen or hydroxyl (—OH); $R^4$ is hydrogen; $R^3$ is hydrogen or is absent; $R^5$ and $R^8$ are hydroxy; and $R^7$ is methoxy; and salts thereof.

All versions of the method include using a compound of Formula (I) wherein $R^3$ is hydrogen. All versions of the method include using a compound of Formula (I) wherein $R^3$ is absent.

It is preferred, but not required, that the concentration of the exogenous imizoquin is from about 0.1 mM to about 0.4 mM. Using concentrations of imizoquin above and below this range is explicitly within the scope of the claimed method.

BRIEF DESCRIPTION OF THE DRAWINGS

FIG. 5A is a graph (germination rate v. hours post-inoculation) showing that the ΔimqK mutant shows a significantly lower rate of germination whereas the OE::imqK mutant shows a significantly higher rate of germination compared to WT strain.

FIG. 5B is a graph (germination rate v. hours post-inoculation) showing that purified imizoquins enhance germination rate in WT. Increasing the imizoquin concentration significantly increases germination rates as compared to control.

FIG. 5C is a graph (germination rate v. hours post-inoculation) showing that imizoquin A restores germination in the ΔimqK mutant in a dose-dependent manner.

FIG. 5D is a graph (germination rate v. hours post-inoculation) showing that imizoquin B restores germination in the ΔimqK mutant in a dose-dependent manner.

FIG. 5E is a histogram showing growth of imqK mutants and WT in GMM media with added $H_2O_2$, t-butyl hydroperoxide (tBOOH) and menadione. Following incubation at 30° C. for 3 days, colony diameters were measured.

FIG. 5F is a histogram showing survival of conidia of ΔimqK, OE::imqK, and WT challenged by incubating spores of each strain with 30 mM of $H_2O_2$. Colonies were counted after incubation at 30° C. for 24 h. Values represent the average of three trials with error bars indicating standard error. The Student's t-test was used to assess statistical significance; *p-value<0.05; p-value<0.01; *p-value<0.001.

DETAILED DESCRIPTION

Figure 1:
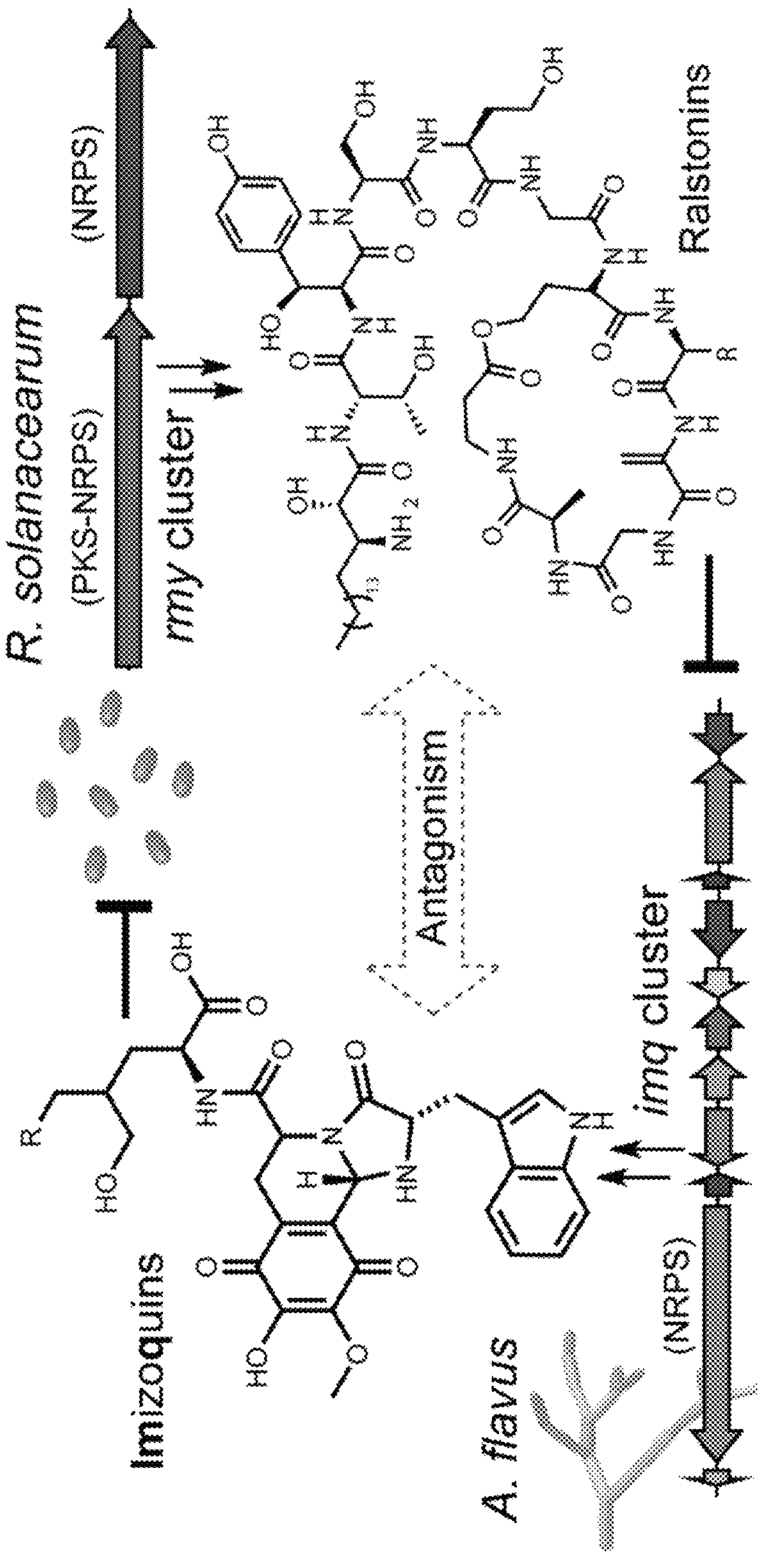
FIG. 1 is a schematic diagram illustrating the antagonism between imizoquins (which stimulate spore germination in *Aspergillus flavus*) and ralstonins (lipopeptides produced by the pathogenic bacteria *Ralstonia solanacearum*, which suppress spore germination).

Abbreviations and Definitions:

ANOVA=analysis of variance.

BGC=biosynthetic gene cluster.

COSY=2-dimensional nuclear magnetic resonance correlation spectroscopy.

HMBC=2-dimensional nuclear magnetic resonance heteronuclear multiple-bond correlation spectroscopy.

NRPS=non-ribosomal peptide synthetase.

OE=overexpression.

"Pharmaceutically-suitable salt"=any acid or base addition salt whose counter-ions are non toxic to the patient in pharmaceutical doses of the salts, so that the beneficial inhibitory effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis b hydroxynaphthoates, gentisates, isethionates, di p toluoyltartrates, methane sulphonates, ethanesulphonates, benzenesulphonates, p toluenesulphonates, cyclohexylsulphamates, quinates, and the like. Base addition salts include those derived from alkali or alkaline earth metal bases or conventional organic bases, such as triethylamine, pyridine, piperidine, morpholine, N methylmorpholine, and the like. See, for example, "Handbook of Pharmaceutical Salts, Properties, Selection, and Use," P. H. Stahl and C. G. Wermuch, Eds., © 2008, Wiley-VCH (Zurich, Switzerland), ISBN: 978-3-90639-058-1.

PKS=polyketide synthase.

WT–wild-type.

All geometric isomers (i.e., cis/trans), stereo isomers (i.e., enantiomers, diastereomers, meso forms), and tautomers, in pure form or in any ratio of enantiomeric or diastereomeric excess, or isomeric enrichment, are explicitly included within the scope of the disclosed and claims.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, and oxygen such as $^2H$, $^3H$, $^{13}C$, $^{14}C$, $^{15}N$, $^{17}O$, and $^{18}O$. Certain isotopically-labeled disclosed compounds (e.g., those labeled with $^3H$ and $^{14}C$) are useful in compound and/or substrate tissue distribution assays. Tritiated and carbon-14 isotopes can allow for ease of preparation and detectability. Further, substitution with heavier isotopes such as deuterium can afford certain functional advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite articles "a" and "an" mean "one or more."

All combinations of method or process steps as used herein can be performed in any order, unless otherwise specified or clearly implied to the contrary by the context in which the referenced combination is made.

The method claimed herein can comprise, consist of, or consist essentially of the essential elements, steps, and limitations of the method described herein, as well as any additional or optional steps, ingredients, components, or limitations described herein or otherwise useful in microbiology or agricultural chemistry.

Ralstonin Downregulates Expression of the imq Gene Cluster in *A. flavus:*

Figure 2A:
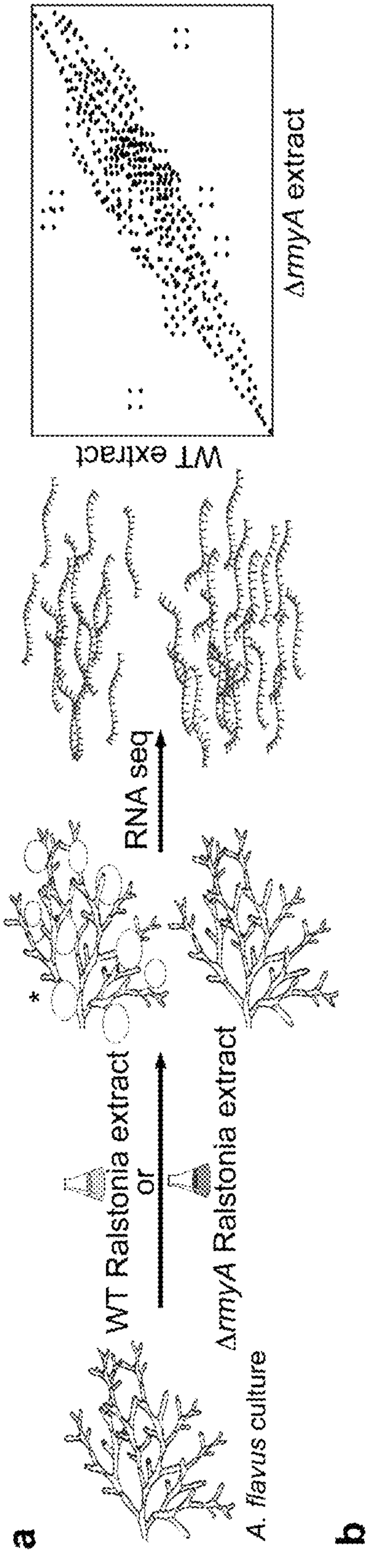
FIG. 2A is a schematic diagram illustrating differential gene expression in *A. flavus* treated with *R. solanacearum* extracts from the wild-type bacteria (WT) (GMI1000, ATCC BAA-1114) or the ArmyA strain of the bacteria.
Figure 2B:
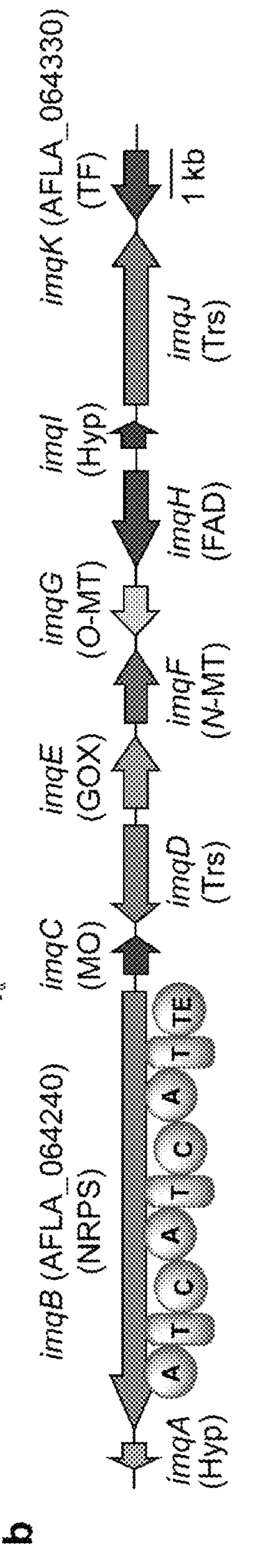
FIG. 2B is a schematic illustration of the imq gene cluster and putative assignments: Hyp: hypothetical protein; NRPS: non-ribosomal peptide synthetase (A=adenylation, T=thiolation, C=condensation, TE=thioesterase domain); MO: phenol 2-monooxygenase; Trs: transporter; GOX: gibberellin oxidase; N-MT: N-methyltransferase; O-MT: O-methyltransferase; FAD: FAD-binding domain protein; TF: transcription factor. **A. flavus* produces chlamydospores—the oval structures in the figure—in response to ralstonin-containing extracts from WT *R. solanacearum.*

Because the ralstonins induce chlamydospore formation in fungi and facilitate bacterial entry into fungal tissues[6], it was hypothesized that these compounds may affect expression of fungal BGCs involved in defense. A comparison was made between RNA sequence data of *A. flavus* treated with either *R. solanacearum* wild-type (GMI1000) extract or ArmyA mutant extract, which is deficient in ralstonin. This comparison is shown schematically in FIG. 2A. Monitoring *A. flavus* gene expression over a 30-hour period differential expression of 65 genes was observed (>2-fold change, false discovery rate-corrected p-value<0.05), of which twenty-nine encoded uncharacterized proteins, eight encoded various transporters, and three encoded putative secondary metabolite genes Supporting Table S1).[8] Two genes down-regulated in GMI1000 vs. ΔrmyA treatment appeared to belong to a cryptic BGC which was designated imq. The imq biosynthetic gene cluster is shown schematically in FIG. 2B. These observations were further confirmed with northern blot analysis (Supporting Figure S1). As shown in FIG. 2B, the imq BGC encodes a canonical three-module NRPS (imqB), a phenol 2-monooxygenase (imqC), two transporters (imqD and imqJ), a gibberellin oxidase (imqE), the N- and O-methyltransferases (imqF and imqG, respectively), a FAD-dependent oxidase (imqH), a C6 transcription factor (imqK), as well as two small proteins with no predicted function (imqA and imqI). The imq cluster is closely related to the wyk BGC in *A. oryzae*, which is involved in the biosynthesis of a family of tripeptide-derived isoquinoline alkaloids.[9,10] Notably, imqC, imqF, and imqH are homologs of fsqG, fsqC, and fsqB, respectively, which we previously showed to carry out the three-step transformation of L-tyrosine into tetrahydroisoquinoline en route to the fumisoquins in *A. fumigatus* via a pathway that is analogous to isoquinoline biosynthesis in plants. See Supporting Table S2.[11]

Figure 3A:
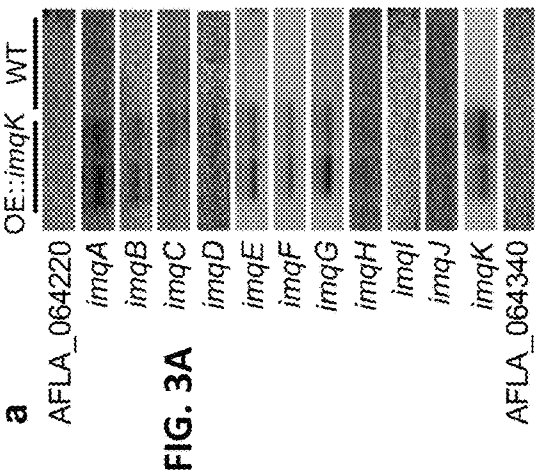
FIG. 3A is a northern blot analysis (i.e., RNA blot analysis) of the imq cluster and flanking genes in OE::imqK and WT *A. flavus* strains.
Figure 3B:
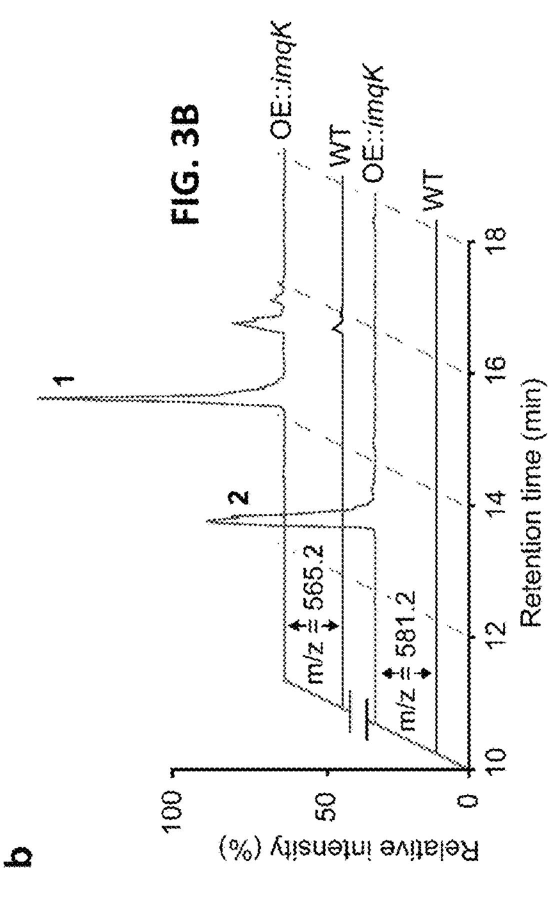
FIG. 3B depicts LC-MS extracted ion chromatograms for imizoquins 1 and 2 in extracts of OE::imqK and WT *A. flavus* strains.
Figure 3C:
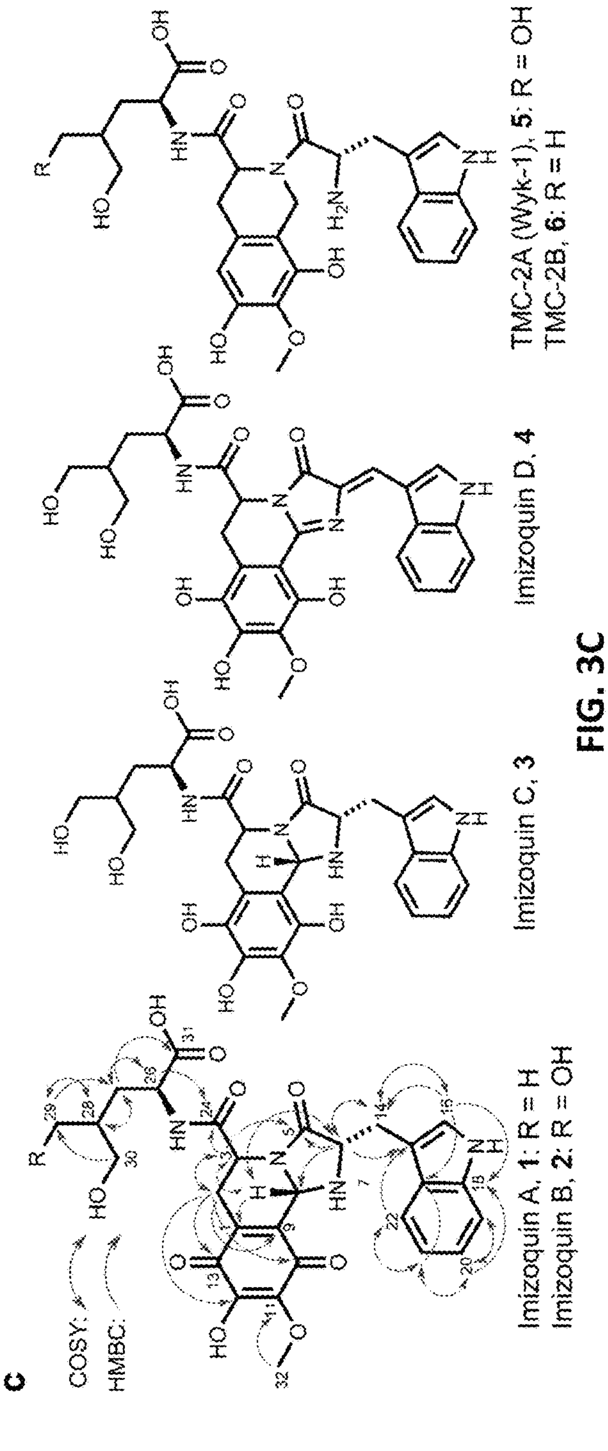
FIG. 3C presents the chemical structures of imizoquins A, B, C, and (compounds 1 through 4) and previously characterized compounds TMC-2A/B (compounds 5 and 6). Key COSY correlations (blue double-headed arrows) and key HMBC correlations from each proton to the indicated carbon (red single-headed arrows) are shown for compounds 1 and 2.

Identification of imq-Derived Metabolites:

To identify imq-derived metabolites an *A. flavus* overexpression (OE) strain was created for the putative C6 transcription factor ImqK[12]. Replacement of the imqK promoter with the constitutively expressed gdpA (OE::imqK) induced expression of the other cluster genes (see the northern blot gels shown in FIG. 3A) and production of a purple pigment (Supporting Figure S2). Two cluster flanking genes (AFLA_064220 and AFLA_064340) were not regulated by ImqK and thus likely define the boundaries of the cluster. Again, see FIG. 3A. To identify imq-derived metabolites, liquid chromatography-mass spectrometry (LC-MS)-based comparative metabolomics[11] of metabolome extracts of OE::imqK and WT *A. flavus* was employed. Because the imq cluster is not expressed in WT under laboratory conditions, any compounds strongly upregulated (or additionally detected) in the OE::imqK strain represented candidates for possible imq-derived metabolites. Six components of the OE::imqK metabolome were detected that were absent in the WT extracts. See FIG. 3B. These six were shown to be compounds 1 through 6, whose structures are provided in FIG. 3C. See also Supporting Figure S3 and Supporting Table S3. Two of these strongly absorb at 420 nm, accounting for the purple pigmentation of OE::imqK cultures. Following chromatographic enrichment, a standard suite of 2D NMR-spectroscopic experiments revealed that these imq-dependent compounds, named imizoquin A and B (1 and 2, respectively; see FIGS. 3B and 3C), represent tripeptide-derived alkaloids featuring the unprecedented imidazo[2,1,-a]isoquinoline ring system. See the Supporting Information for structural elucidation details. The molecular formulae of two additional imq-dependent compounds differed from that of imizoquin B (2) by +/−2.016, corresponding to two hydrogen atoms (Supporting Table S3), suggesting that these compounds, named imizoquin C and imizoquin D (3 and 4, respectively), represent different oxidation states of the same scaffold, which was confirmed by 2D NMR spectroscopic analysis (Supporting Tables S6-S9). The remaining two imq-dependent metabolites were identified as the previously described isoquinoline alkaloids TMC-2A/B[13] (compound 5 and 6, FIG. 3C and Supporting Figure S3), which likely represent intermediates in the biosynthesis of the fused tricyclic imidazo[2,1-a]isoquinoline ring system of compounds 1 through 4.

Figure 4:
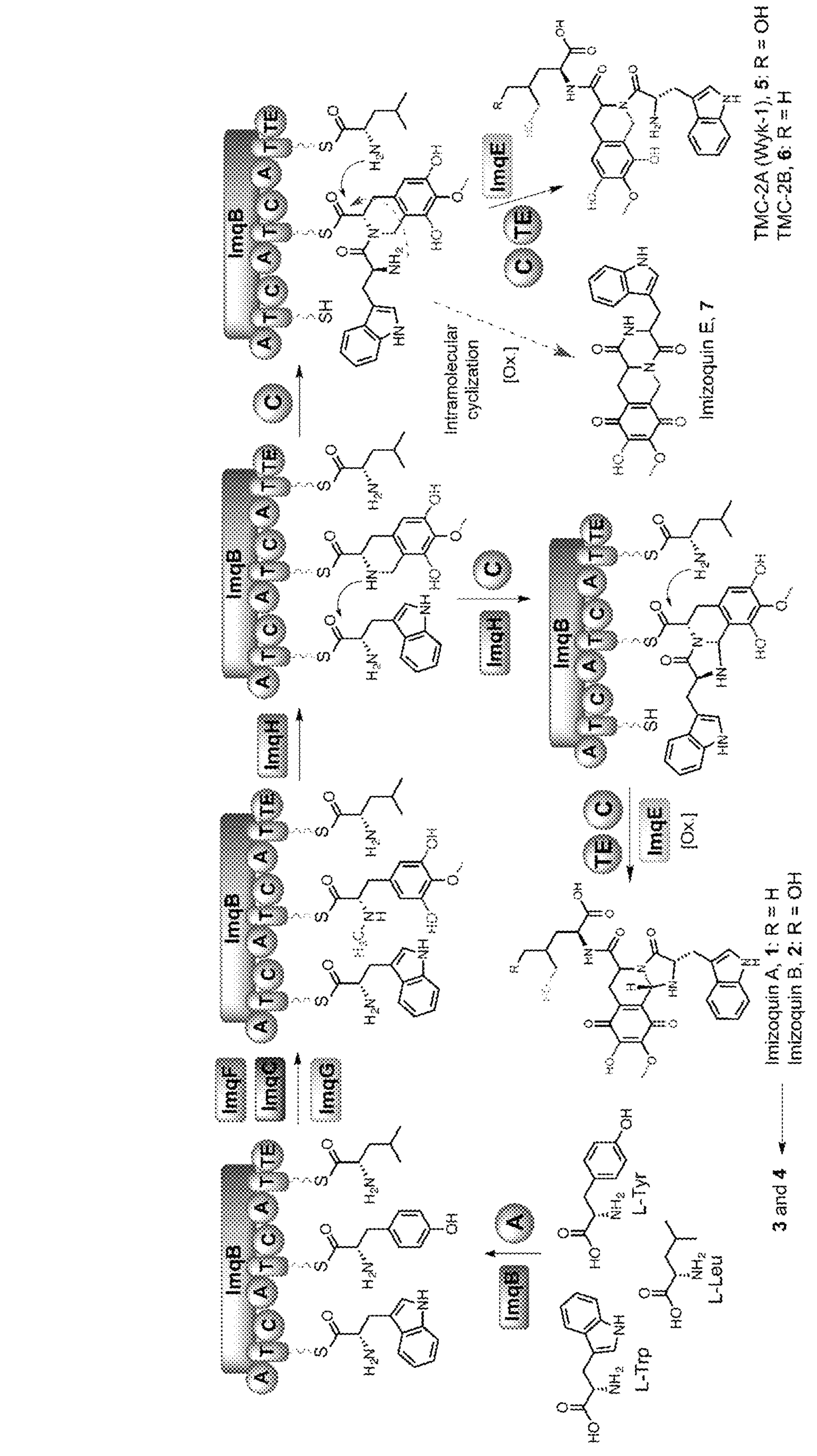
FIG. 4 is a schematic diagram of the proposed route for imq biogenesis. ImqB (NRPS, green), ImqF (N-methyltransferase, pink), ImqC (phenol 2-monooxygenase, purple), ImqG (O-methyltransferase, yellow), ImqH (FAD-dependent oxidase, blue), ImqE (gibberellin oxidase, turquoise), A (adenylation domain), T (thiolation domain), C (condensation domain), TE (thioesterase domain), and Ox. (oxidation).

Additional Metabolic Profiling and a Model for Imizoquin Biogenesis:

Without being bound to any underlying mechanism or biological phenomena, ImqB is a canonical three-module NRPS. This suggests that assembly of the tripeptide backbone of the imizoquins occurs by standard NRPS assembly line-style adenylation, thiolation, and condensation of Trp, Tyr, and Leu derived precursors.[14] This proposed process is illustrated schematically in FIG. 4. ImqC, imqF, and imqG are close homologs of the tailoring genes responsible for isoquinoline formation in the *A. fumigatus* fsq cluster,[11] suggesting that isoquinoline formation en route to the imizoquins proceeds as described for the case of fsq-derived metabolites, including N-methylation (by ImqF) and phenol oxidation (by ImqC), followed by cyclization via the FAD-dependent oxidase ImqH. Again, see FIG. 4, and also Supporting Figure S4). Importantly, this sequence of steps requires the presence of a free amine in the tyrosine moiety, indicating that isoquinoline formation occurs prior to peptide bond formation. This biosynthetic model is further supported by the identification of an additional imq-dependent metabolite, the pyrazino[1,2-b]isoquinoline 7 (imizoquin E, see Supporting Table S3 for HR-MS and Supporting Table S10 for NMR spectroscopic data), which likely arises from nucleophilic attack of the Trp-derived amino group onto the thioester-attached dipeptide intermediate, as shown in FIG. 4. In this model, the imidazolidin-4-one ring could form following additional oxidation of the methyl-derived bridgehead carbon by ImqH. Lastly, O-methylation (by ImqG) and leucine hydroxylation (by ImqE) complete biosynthesis of the imizoquins.

Figure 5B:
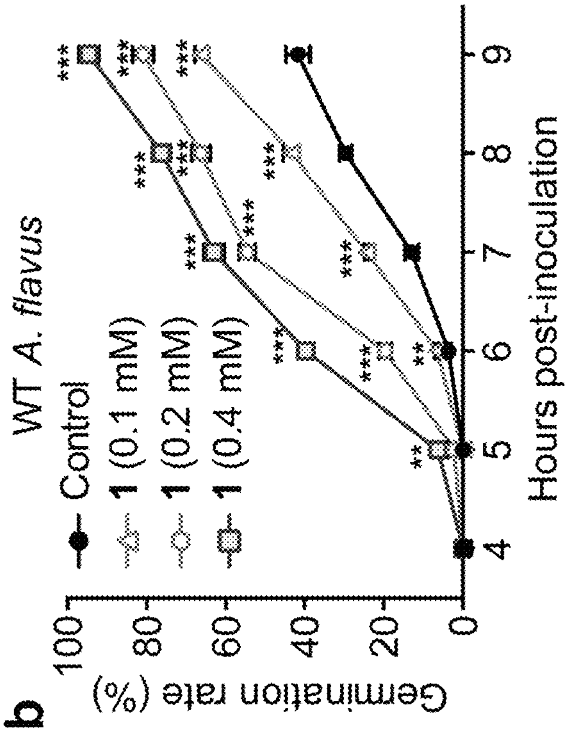
FIGS. 5A-5F are a series of graphs showing that imizoquins promote germination and provide resistance to reactive oxygen species. Purified imizoquins enhance germination rate in WT fungi in a dose-dependent fashion. Increasing the imizoquin concentration significantly increases germination rates as compared to control. The germination rate of imqK strains was tested between 4 to 9 hours post-inoculation (hpi) in glucose minimal media. Appearance of a germ tube indicated the onset of germination.
Figure 5A:
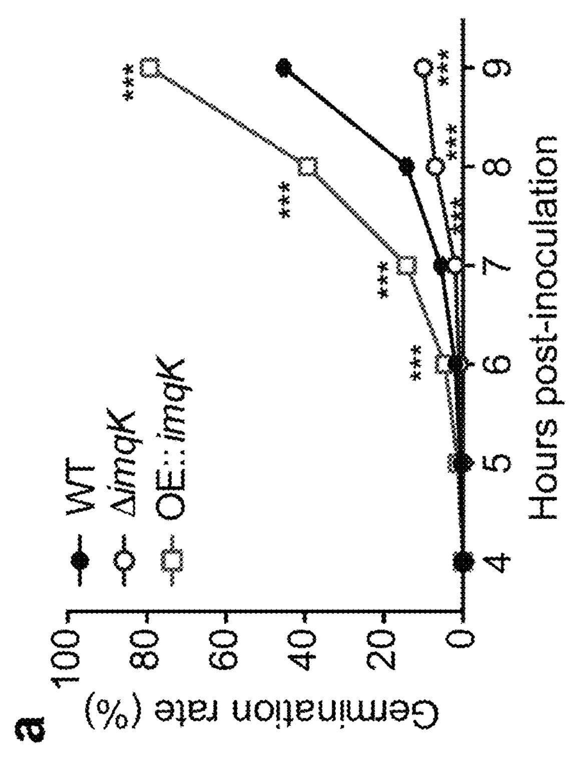
Figure 5D:
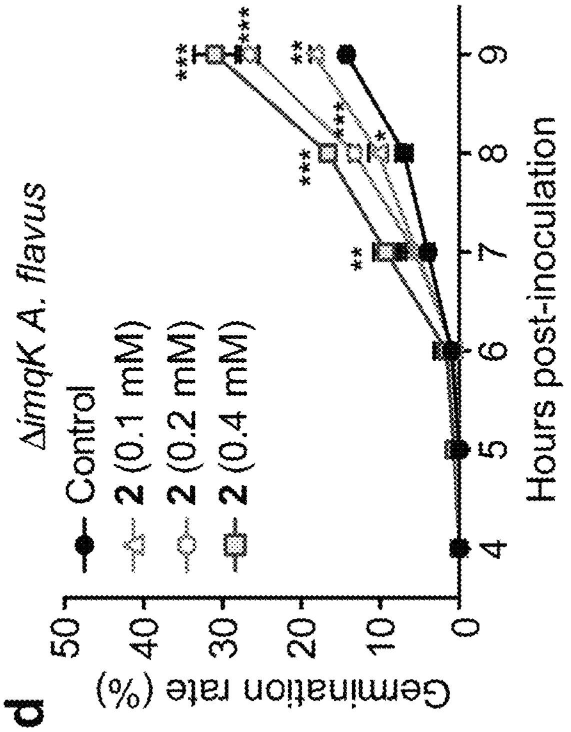
Figure 5C:
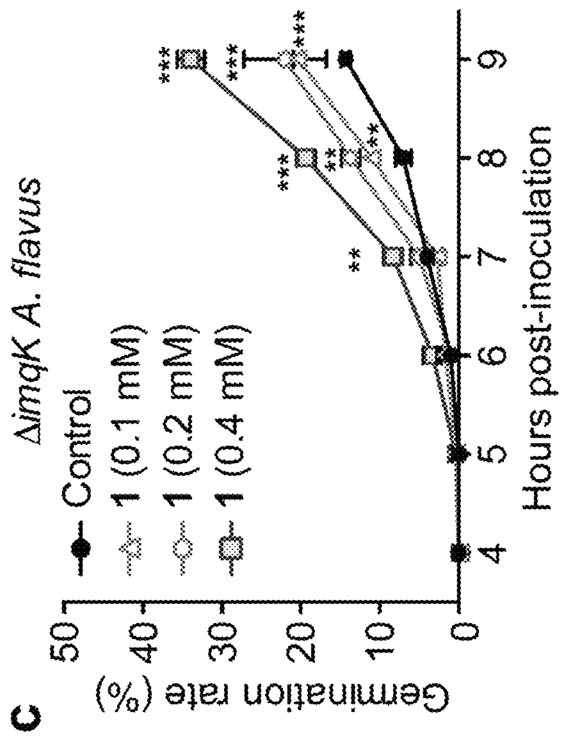

Imizoquins are Required for Normal *A. flavus* Germination:

With the exception of a purple pigmentation observable in the OE::imqK mutant, the ΔimqK and OE::imqK strains showed little differences from wild-type (WT) in vegetative growth (Supporting Figure S2). However, in assessing the strains for any developmental changes, a consistent pattern of delayed germination in ΔimqK and accelerated germination in OE::imqK compared to WT was seen, such that by 9 hours post-inoculation (hpi) ca. 80% of OE::imqK spores had germinated compared to 40% of WT and only 10% of ΔimqK. See the graph of FIG. 5A and Supporting Figure S5). To test whether these differences in germination rates were a result of differences in imizoquin production, purified imizoquins were added to ΔimqK and WT *A. flavus* cultures and their germination rates were measured. Imizoquin A and B (1-2) were added to spores at 0.1 mM, 0.2 mM, and 0.4 mM. As shown in the graphs of FIGS. 5B, 5C, and 5D, at all tested concentrations the imizoquins increased germination of both ΔimqK and WT to above that of untreated OE::imqK (imizoquin B (2) was only tested on ΔimqK). This occurred in a dose-dependent fashion up to approximately 0.4 mM. Concentrations above 0.4 mM did not further increase the germination rate (Supporting Figure S6). Testing of the structurally related alkaloids, TMC-2A and TMC-2B (5 and 6, respectively)[13], showed similarly accelerated germination (Supporting Figure S7). While imizoquin biosynthesis is required for germination, these compounds are not sequestered in the spore, as evidenced by LC-HRMS metabolite profiling of 1-7 in isolated conidia vs. isolated mycelia (Supporting Figure S3). This suggests that imizoquin biosynthesis is activated early in the process of initiation of germination, as shown below.

Imizoquin Induction of Germination is Conserved in Fungal Species:

Imizoquins were shown to promote germination rates in other fungi, in addition to *A. flavus*. Supporting Figure S8 shows that compound 1 increases the germination rate of all tested *Aspergillus* species, including the *A. oryzae* and the more phylogenetically distant *A. nidulans* and *A. fumigatus*. Additionally, 1 increased the germination rate of *Penicillium expansum* (a species in the order Eurotiales). As observed with *A. flavus* (Supporting Figure S6), the effect was dose-dependent up to about 0.4 mM. Concentrations above 0.4 mM did not further increase germination rates.

Figure 5F:
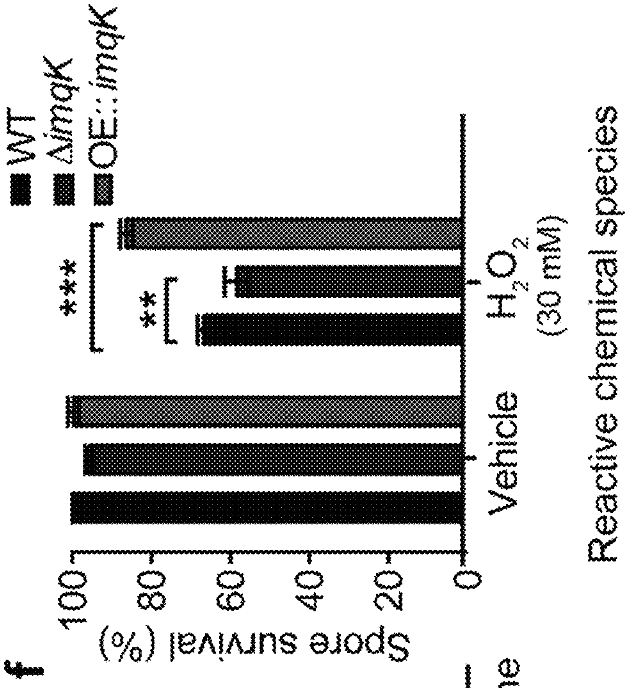
Figure 5E:
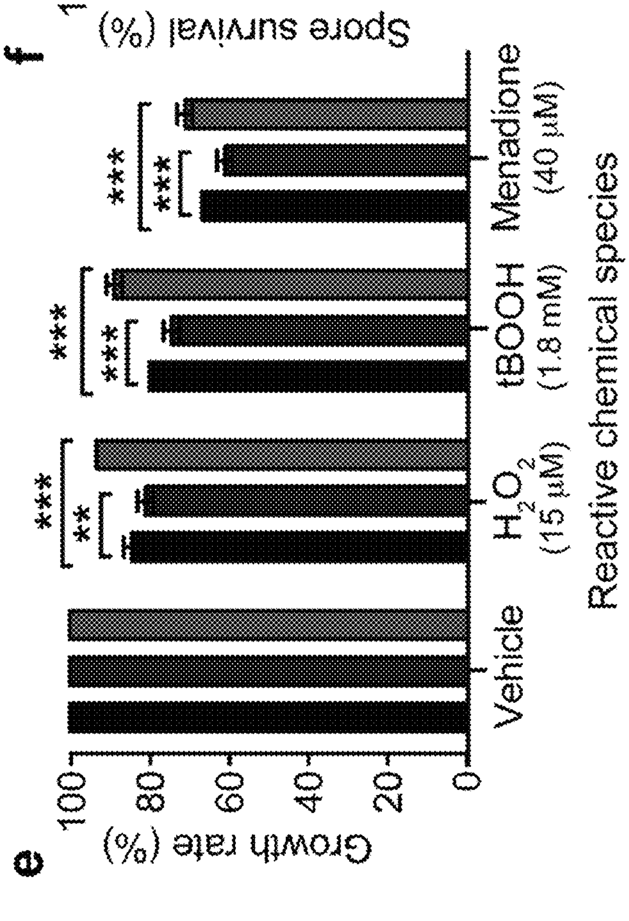
Figure 6A:
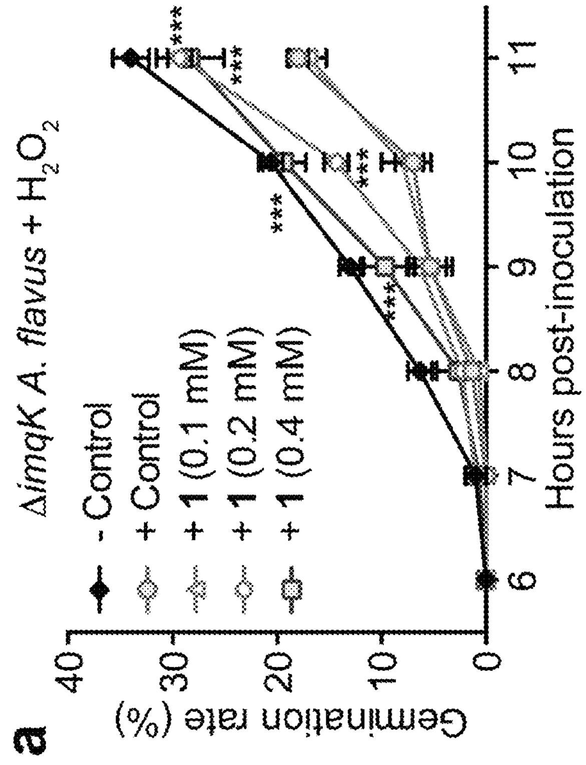
FIG. 6A is a graph depicting the antioxidant properties of the imizoquins in the ΔimqK strain. The cells were treated with different concentrations of compound 1 in the presence of 0.7 mM $H_2O_2$, and their germination rate was measured over time. Imizoquin A (1) counteracted the germination inhibitory activity of $H_2O_2$. Statistical significance is indicated as compared to positive control.
Figure 6B:
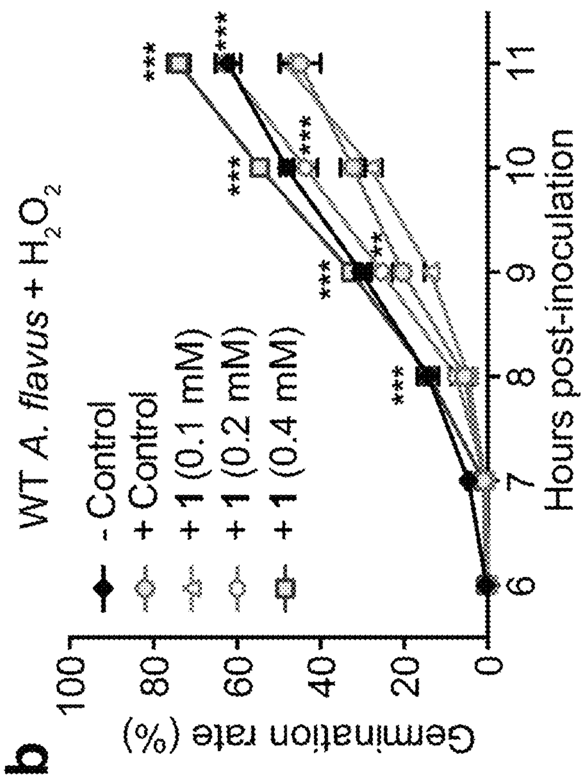
FIG. 6B is a graph depicting the antioxidant properties of the imizoquins the WT strain. The cells were treated with different concentrations of compound 1 in the presence of 0.7 mM $H_2O_2$, and their germination rate was measured over time. Imizoquin A (1) counteracted the germination inhibitory activity of $H_2O_2$. Statistical significance is indicated as compared to positive control.
Figure 6C:
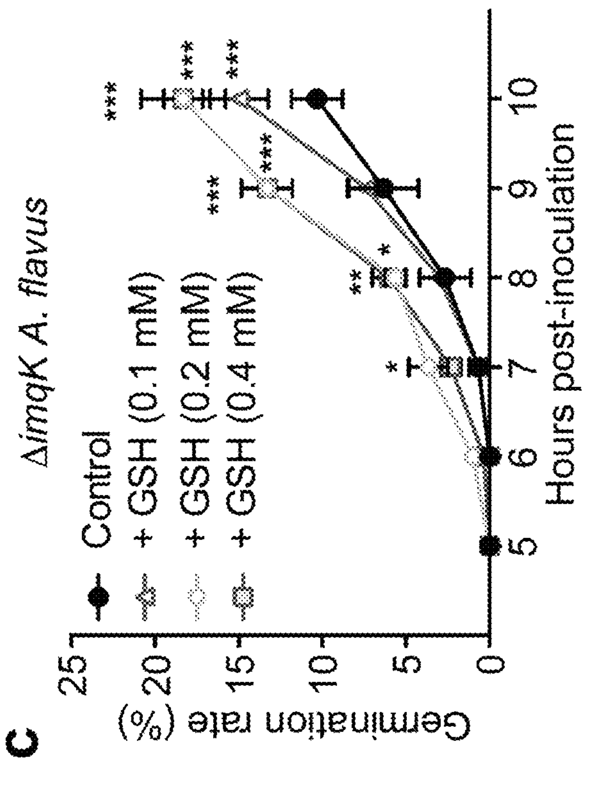
FIG. 6C is a graph showing the effect of glutathione (GSH) on germination in the ΔimqK mutant. All tested concentrations of GSH significantly promoted germination rate in the ΔimqK mutant. Values represent means of three replicates ±standard errors. Asterisks indicate statistical significance according to one-way analysis of variance ("ANOVA") followed by Tukey's post-hoc test; *p-value<0.05, p-value<0.01, *p-value<0.001.
Figure 6D:
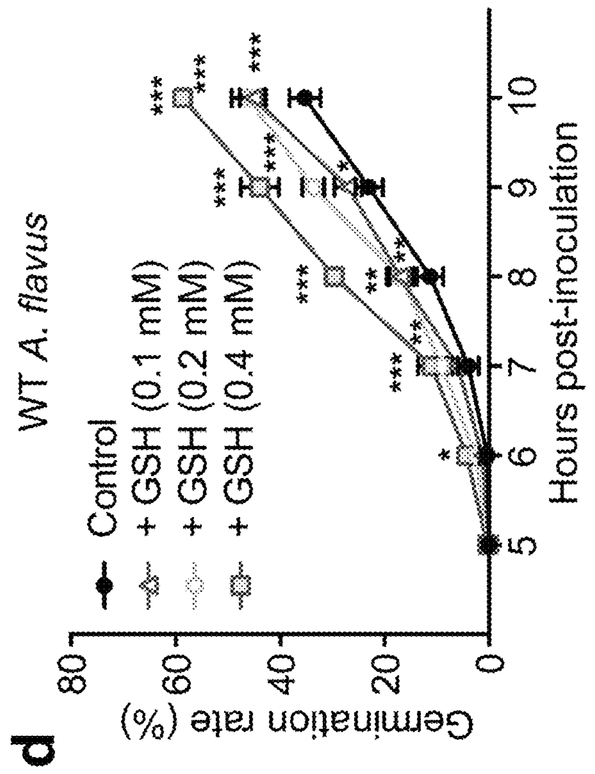
FIG. 6D is a graph showing the effect of glutathione (GSH) on germination in the WT. All tested concentrations of GSH significantly promoted germination rate in the WT. Values represent means of three replicates ±standard errors. Asterisks indicate statistical significance according to one-way ANOVA followed by Tukey's post-hoc test; *p-value<0.05, p-value<0.01, *p-value<0.001.

Imizoquins Induce Germination Through a ROS-Dependent Mechanism:

Fungal spore germination is affected by many different, interacting parameters, e.g. density, temperature, growth medium composition, etc.[15,16] However, the identification of a specific family of metabolites that accelerate germination provided an opportunity to investigate mechanisms underlying germination. Because the structures of the imizoquins suggest that they may serve a role in fungal redox chemistry, the resilience of the OE::imqK and ΔimqK mutant strains to oxidative stress induced by hydrogen peroxide[17], t-butyl peroxide, and menadione was tested. Growth rates were evaluated, as well as spore survival (for hydrogen peroxide only). The results are depicted in FIGS. 5E and 5F. In comparison to wild type it was found that the OE::imqK strain showed increased resistance to several reactive oxygen species-(ROS) generating treatments, whereas the ΔimqK strain exhibited enhanced ROS sensitivity in both mycelial growth (FIG. 5E) and spore survival (FIG. 5F) assays. Comparing imizoquin A and B (1 and 2, respectively) to a known antioxidant, uric acid, it was found that both compounds exhibited significant antioxidant activities (Supporting Figure S9), and, furthermore, protected spores from the germination inhibitory effects of $H_2O_2$. See FIGS. 6A and 6B. The related metabolites, TMC-2A/B (compounds 5 and 6), also showed antioxidant properties. See Supporting Figure S9. These data suggested that the pro-germination properties of the identified imq-dependent compounds are due to ROS quenching. To further examine this hypothesis, an alternative antioxidant, glutathione, was tested to see if it could promote germination. Similar to the imizoquins, exogenously added glutathione promoted the germination rate of both ΔimqK and WT strains in a concentration-dependent manner. The results are shown in FIGS. 6C and 6D, respectively.

To test whether ROS is involved in activation of the imq cluster, the expression of imq genes was measured before, during and after germination by semi-quantitative RT-PCR, with and without the addition of a ROS source in WT *A. flavus* (Supporting Figure S10). It was found that imq cluster expression is activated during early germination but does not appear to be affected by the addition of ROS. Taken together the data indicate that imizoquins produced early in the germination process underlie the observed ROS protection, but that the upregulation of the imq cluster in *A. flavus* upon contact with *R. solanacearum* is triggered by the ralstonins and not ROS.

Figure 7A:
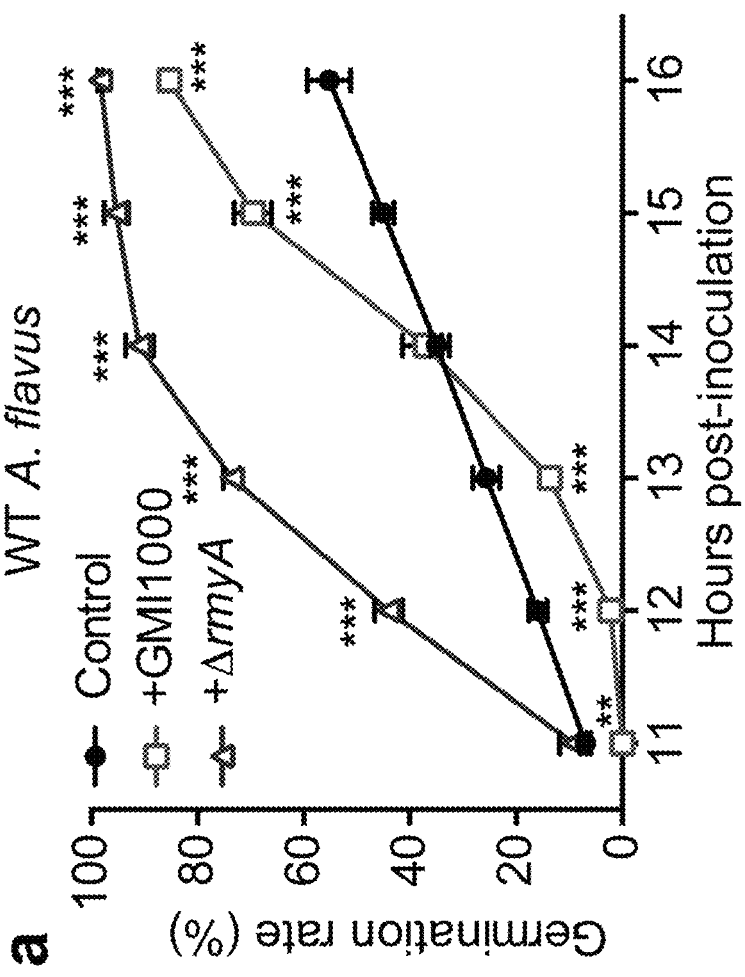
FIG. 7A is a graph showing that *R. solanacearum* extracts (GMI1000 and ΔrmyA) affect *A. flavus* germination. Conidia suspensions ($1\times10^5$ spores $mL^{-1}$) of different *A. flavus* strains were treated with extracts of WT *R. solanacearum* (GMI1000) and the ΔrmyA mutant. Germination rates were assessed 11 to 16 hours post-inoculation. In WT *A. flavus*, extracts from the ΔrmyA mutant significantly enhanced germination rates at all time points, whereas GMI1000 extracts decreased germination rates at earlier and increased rates at later time points.
Figure 7B:
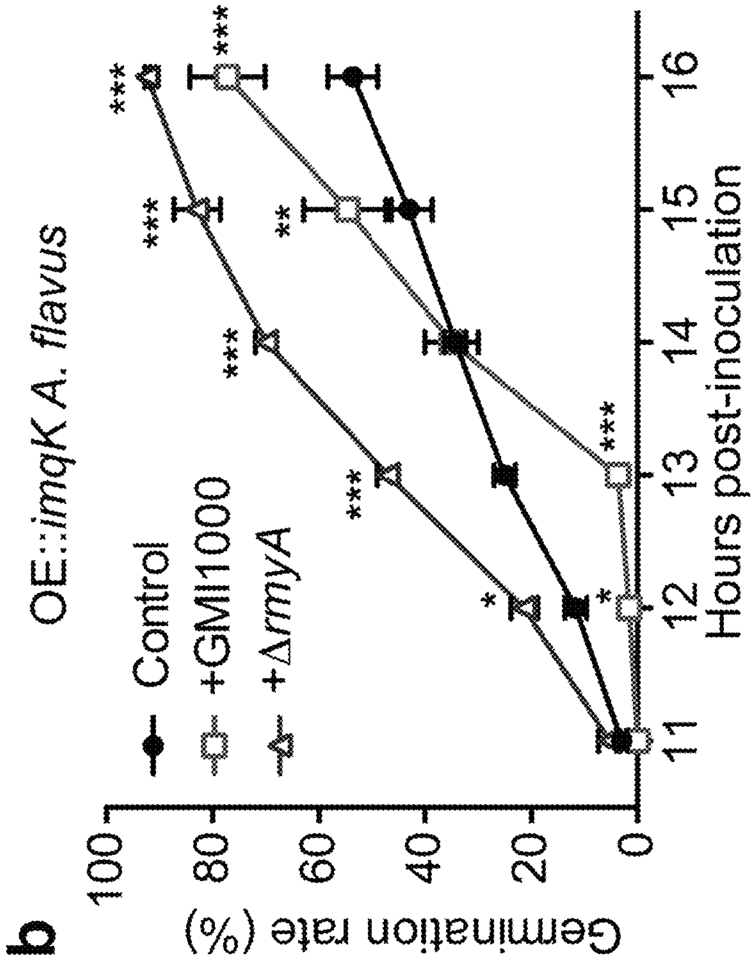
FIG. 7B is analogous to FIG. 7A, but using the OE::imqK strain. As seen in the graph, OE::imqK germination rates were similar to the WT strain.
Figure 7C:
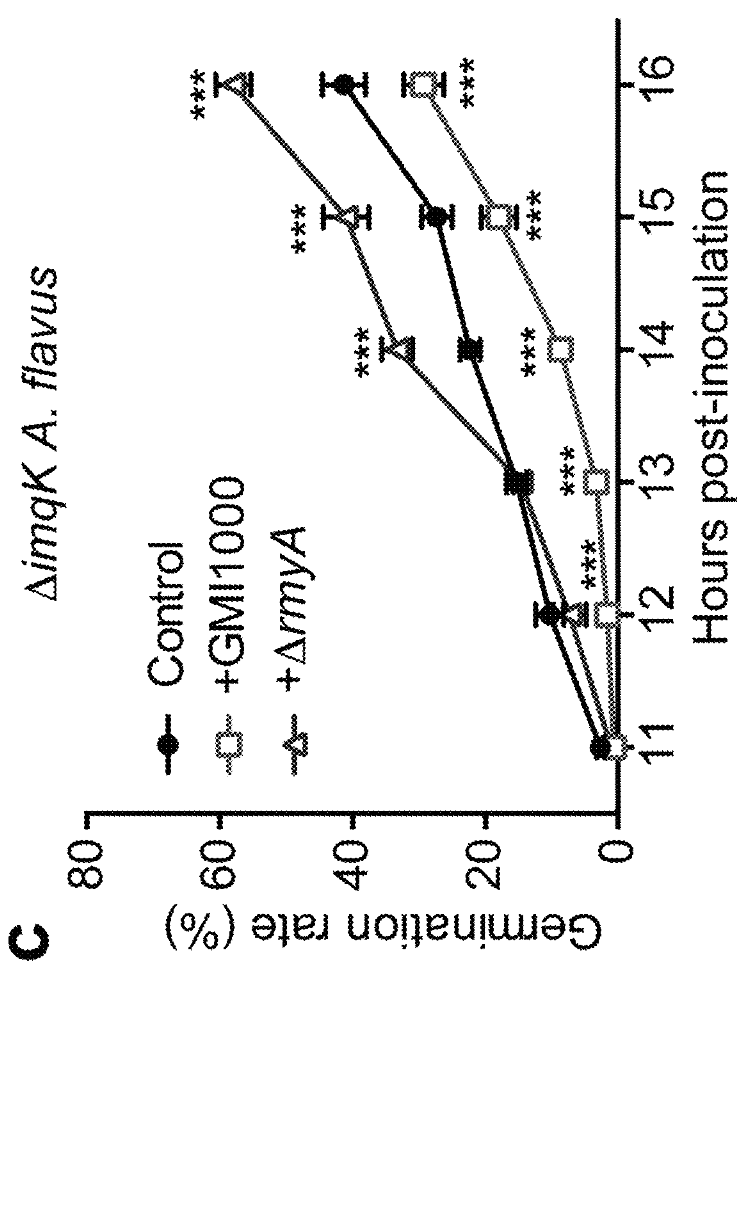
FIG. 7C is analogous to FIG. 7A, but using the ΔimqK strain. For the ΔimqK mutant, ΔrmyA extracts promoted germination at later time points, whereas GMI1000 extracts consistently delayed germination. For FIGS. 7A, 7B, and 7C, values represent average of three trials±standard error. Asterisks indicate the statistical significance (relative to the control) according to the Student's t-test; *p-value<0.05; p-value<0.01; *p-value<0.001.

Impacts of Imizoquins on *Ralstonia* Replication and Ralstonin on *Aspergillus* Germination:

Based on the results of the transcriptomic analysis, which showed that that imq cluster expression is downregulated in response to GMI1000 relative to ΔrmyA extracts, it was hypothesized that the ralstonins, by suppressing imq cluster expression, negatively affect fungal germination. To assess potential effects of the ralstonins, ralstonin-containing GMI1000 extracts were examined for any effect on spore germination. GMI1000 extracts initially delayed germination of all three strains of *A. flavus* compared to the methanol control. See FIGS. 7A (WT *A. flavus*) 7B (OE::imqK *A. flavus*), and 7C (ΔimqK), (Note that incorporation of methanol in the extracts delayed even germination of the control strain to 11 hpi). However, germination rates of both the WT and OE::imqK mutant exceeded that of methanol control after 14 hours in the case of GMI1000 extract, whereas germination rates of the imizoquin-deficient ΔimqK strain remained lower than control. In contrast, extracts from the ralstonin-deficient ΔrmyA strain promoted germination of all three strains of *A. flavus* in comparison to both methanol control and GMI1000 extracts. These results suggest an inhibitory effect of ralstonin on spore germination that is counteracted in part by induction of the imizoquin pathway.

Conversely, the imizoquins might adversely affect *R. solanacearum* growth. Therefore, purified imizoquins were tested for their effect on bacterial replication. Supporting Figure S11 shows that imizoquin treatment decreases *R. solanacearum* growth modestly at 24 hours, with the ArmyA mutant strain being more sensitive to 1-2 than WT (GMI1000). At 48 hours, we observe reduced inhibition of *R. solanacearum* growth by imizoquin treatment, except for the case of imizoquin A in the ΔrmyA mutant, which could result from variable degradation of the easily oxidizable imizoquins, Nonetheless, these data suggest that imizoquin production favors fungal growth over that of bacteria.

Conclusions

Although genome sequencing reveals that BGCs account for a significant fraction of microbial genomes, biological functions of only a small portion of known BGC-derived metabolites have been explored. Significantly, the mechanisms by which these compounds impact growth and development of other microbes in shared environments is largely uncharted. Here alkaloids derived from fungal BGC imq have been characterized and shown to function as an essential germination stimulatory signal with additional antibacterial properties. Their specific properties suggest that imizoquin and related isoquinolines may provide competitive advantages to *A. flavus* and other closely related fungi in rhizosphere encounters.

The imizoquins appear to promote spore germination through their antioxidant properties. Sensitivity and resistance to ROS was correlated with loss and over expression of imqK and concomitant loss and increase in imizoquin production. Both exogenous addition of imizoquins and the related isoquinolines TMC-2A/B increased spore germination as did the antioxidant glutathione. ROS-protective properties may be a general feature of quinolones and isoquinolines, as recent preclinical studies with plant isoquinolines such as berberine and neferine have reported on their anti-ROS activities as part of the mechanisms underlying therapeutic efficacy[18-20].

Endogenous antioxidants such as the imizoquins may represent developmental cues enabling the fungus to respond to environmental stresses including ROS challenges in a manner ensuring survival. ROS are known to impact fungal differentiation in several different ways. For example, redox metabolites produced by *Pseudomonas aeruginosa* induce *Aspergillus* sporulation along a diffusion gradient[21]. ROS synthesis, in association with the RacA GTPase/NADPH oxidase (Nox complex), was found indispensable for phialide elongation and other cellular morphogenesis mechanisms in *A. fumigatus*[22]. On the other hand ROS accumulation can hinder spore germination[23-25]. In general then, to initiate the process of germination, a set of genes/cellular machinery is required to overcome and adapt to ROS stress. For example, at early stages of germination, conidia express enzymes that are involved in detoxification of ROS[26], and deletion of ROS detoxification genes can result in delayed germination in fungi[27]. Furthermore, in *A. nidulans*, deletion of the gene for glutathione reductase (GR), the enzyme required for the production of intracellular reduced glutathione (GSH), resulted in germination defects and an abnormal cell growth pattern that was compensated by adding GSH into the growth medium[28].

These examples show that fungi rely on multiple strategies to maintain ROS levels appropriate for spore germination. However, whereas canonical ROS defense response pathways and glutathione generation are conserved in all fungi, ROS protection by secondary metabolites might be species-specific and possibly evolved in response to specific environmental challenges, e.g. competition with bacteria. In addition to our work presented here, other studies have documented inhibition of spore germination by bacterial and plant natural products[29,30] including the lipopeptide iturin A[31]. Thus, it would make sense evolutionarily for fungi to develop spore protective mechanisms and, conversely, for opposing organisms to silence these mechanisms. Considered together, our data suggest that fungal imizoquins represent yet one more ROS protective mechanism that may be particularly responsive to encounters with competing microbes.

EXAMPLES

Fungal and Bacterial Strains and Culture Conditions:

All the strains used are listed in Supporting Table S4 and detailed fermentation conditions are in the methods section of the Supporting Information, attached hereto and incorporated herein by reference.

Analytical Methods and Equipment Overview:

Detailed information about the instrumentation, software packages, and methods used for NMR spectroscopy, analytical low- and high-resolution HPLC-MS, and semi-preparative HPLC for compounds 1-7 is in the Supporting Information.

Gene Cloning, Plasmid Construction, and Genetic Manipulations:

Detailed information about the methods used for gene cloning, plasmid construction, and genetic manipulations is in the Supporting Information. The oligonucleotide sequences for PCR primers are given in Supporting Table S5. All strains were verified by PCR and Southern blot analysis (Supporting Figure S12).

Northern analysis: 50 mL of liquid GMM[32] were inoculated with $1.0\times10^6$ spores (asexual) $mL^{-1}$ of all appropriate strains in this study and incubated with shaking at 250 rpm at 25° C. After 48 h, the mycelium was collected and total RNA was extracted by using Isol-RNA Lysis Reagent according to the manufacturer's instructions (5 Prime).

Germination Assay: Each strain was grown in triplicate in 2 mL of liquid GMM inoculated with $1\times10^5$ spores $mL^{-1}$ in a well of a sterile Costar® 12-well plate (Corning) and incubated at 30° C. in OKO-Lab microscopic enclosure equipped with a Nikon Eclipse Ti inverted microscope. Germinated spores were observed using a Nikon Plan Fluor 20xPh1 DLL objective and phase-contrast microscope. A spore was considered germinated when the length of the spore protrusion (emerging hyphal tip) exceeded the spore's diameter[15,33]. Images were captured hourly using the Nikon NIS Elements AR software package (v. 4.13), and the germination rate was determined by counting germlings per hundred spores. The experiment was repeated three times.

Germination Assay with Purified Imizoquins. Compounds 1-2 were assessed for their effect on germination of different fungal strains. Each metabolite was dissolved in methanol at a starting concentration of 10 mg $mL^{-1}$ and stored at −80° C. Sterile Costar® 96 well plates containing 100 μL of GMM supplemented with various concentrations of purified 1-2 (0.1 mM, 0.2 mM, 0.4 mM, 0.8 mM and 1.2 mM) were inoculated at $1\times10^5$ spores/well. Spores treated with equivalent volumes of the carrier (methanol) served as negative controls for each experiment. The germination rate (%) was measured as above with each treatment assayed in triplicate.

Reactive Oxygen Species (ROS) Stress Assays:

Mycelial ROS Assay: To determine the relative tolerance of WT and mutant imqK strains to oxidative stress, a range of concentrations of three oxidants were used following the methods of Bok et al.[34]. Briefly, 5 μL of freshly-grown (seven days old) $1\times10^5$ spores $mL^{-1}$ of each strain were inoculated onto solid GMM which had been supplemented with $H_2O_2$ (5 μM, 10 μM, or 15 μM), tertiary butyl hydroperoxide (tBOOH; 0.6 mM, 1.2 mM, or 1.8 mM), or menadione (20 μM, 30 μM, or 40 μM). GMM without any stressor served as control. The plates were incubated at 29° C. and colony diameters were measured after three and six days of incubation. All treatments were assayed in triplicates.

Spore ROS assay: To compare spore viability of ΔimqK and OE::imqK mutants with WT strain under $H_2O_2$ (Sigma-Aldrich) stress the procedure of Qin et al. (2011) was followed with slight modifications[35]. Spore suspensions obtained after 7 days of growth were used to make dilutions in 0.01% Tween 80 in water. These dilutions ($1\times10^6$ spores $mL^{-1}$) were exposed to different concentrations of $H_2O_2$ (0, 10 mM, 15 mM, or 30 mM) for 30-90 minutes. The 30 mM concentration of $H_2O_2$ gave 50% spore survival after 60 minutes of incubation and was used in subsequent assays. After incubation for 60 minutes at 29° C., spores were washed twice by centrifugation (1500×g for 2 min.) and resuspension in 1 mL of distilled $H_2O$. The washed spores were diluted and 100 μL of $1\times10^3$ spores $mL^{-1}$ were spread on GMM plates. Plates were incubated at 29° C. and observed for number of colonies formed after 24 and 48 hrs. Three replicates were performed for all conditions.

Germination ROS assay: To estimate the effect of $H_2O_2$ on germination of mutant and WT strains; 100 μL of GMM, containing freshly harvested spores ($1\times10^5$ spores $mL^{-1}$), were treated with different concentrations of $H_2O_2$ ($10^{-12}$ to $10^{-2}$ M;[36] in triplicate in sterile Costar® 96 well plate at 30° C. GMM without $H_2O_2$ was used as control. The germination rate (%) was measured for the 9 h time point.

For one concentration of $H_2O_2$ (0.7 mM) three different concentrations of imizoquin A (0.1 mM, 0.2 mM, 0.4 mM) were added to the treatment to assess germination. Treatment with $H_2O_2$ only was the positive control and treatment with either 1 or $H_2O_2$ was used as the negative control. Each treatment was performed in triplicate.

Antioxidant Assay: ROS quenching potential of the imizoquins was analyzed using the OxiSelect™ Total Antioxidant Capacity Assay Kit (Cell Biolabs, Inc., San Diego, Calif.) following the manufacturer's instructions. Briefly, 20 μL of diluted uric acid standards (0-1 mM) and imizoquins (0-1 mM) were combined with 180 μL of 1× reaction buffer/well in a Costar® 96 well plate. After mixing thoroughly, an initial absorbance was obtained at 490 nm using a BioTek EPOCH 2 microplate reader with Gen5 acquisition software. Then 50 μL of the 1× copper ion reagent was added into each well and the plate was incubated for 5 minutes on an orbital shaker. To terminate the reaction, 50 μL of 1× stop solution was added and the final absorbance was measured again at 490 nm.

Germination Assay with Antioxidant: Conidia suspensions of imqK mutants and WT strain ($1\times10^5$ spores $mL^{-1}$ of water containing 0.01% Tween 80) were treated with three different concentrations (0.1 mM, 0.2 mM, or 0.4 mM) of glutathione (GSH) in GMM and incubated at 30° C. The number of germinated spores out of hundred spores was counted hourly 5-10 hours post-inoculation (hpi). Three independent replicates were analyzed for each treatment.

*Aspergillus/Ralstonia* Interactions: Metabolite extraction of *R. solanacearum* strains (GMI1000 and ΔrmyA) was carried out following the protocol of Spraker et al. (2016)[6]. Briefly, overnight liquid cultures of both GMI1000 and ΔrmyA strains were inoculated into 500 mL of CPG containing 10 g of Amberlite XAD-16 resin (Sigma-Aldrich) for three days at 30° C. and 200 rpm. The resin was then vacuum filtered and washed twice with 500 mL of double-distilled $H_2O$ to remove cellular debris and excess salts. The adsorbed metabolites were then eluted with 1:1 methanol/dicholoromethane and the organic fraction was dried using vacuum centrifugation (Büchi R-210 Rotavapor Rotary Evaporator, Vacuum Controller V-500). Subsequently, these crude extracts were reconstituted in 100% methanol.

The germination assay was used to test the impact of the crude extracts of GMI1000 and ΔrmyA on the growth of WT and mutant imqK strains. Each test strain, inoculated in 100 μL of GMM, was treated with 10 μL of the crude methanolic extract in well of a sterile Costar 96 well plate maintained at 30° C. Tests were performed in triplicate, and 10 μL of methanol served as the control treatment. Due to solvent effect, germination rate was measured hourly at 11-16 hours of incubation.

Growth Inhibition of *R. solanacearum* in the Presence of Imizoquins:

Overnight liquid cultures of *R. solanacearum* strains (GMI1000 and ΔrmyA) were pelleted by centrifugation at 11,000 rpm, washed twice in equal volumes of sterilized, double-distilled water, quantified and adjusted to $OD_{600}$ of 0.1. Imizoquin A (1) and imizoquin B (2) were added to CPG medium (0.4 mM final concentration of each metabolite) in wells of a sterile Costar® 96 well plate. Then 5 μL of bacterial suspension was added in each well to make a final volume of 100 □L/well. Equal volume of methanol in CPG was used as a control. $OD_{600}$ and $OD_{450}$ were measured after 0, 12, 24 and 48 hours of incubation at 30° C. Measured values from time 0 were subtracted from subsequent time point values to normalize for absorbance by imizoquins.

Statistical analyses: Statistical differences of data were analyzed using GraphPad Prism 7 software package (GraphPad Software Inc., La Jolla, Calif.). p-values were calculated with one way ANOVA for multiple comparisons.

REFERENCES CITED (1) Tarkka, M. T., Sarniguet, A., and Frey-Klett, P. (2009) Inter-kingdom encounters: recent advances in molecular bacterium-fungus interactions. *Curr. Genet.* 55, 233-243.

(2) Schrey, S. D., Erkenbrack, E., and Frith, E. (2012) Production of fungal and bacterial growth modulating secondary metabolites is widespread among mycorrhiza-associated streptomycetes. *BMC Microbiol.* 12, 164.

(3) Netzker, T., Fischer, J., Weber, J., Mattern, D. J., Konig, C. C., Valiante, V., Schroeckh, V., and Brakhage, A. A. (2015) Microbial communication leading to the activation of silent fungal secondary metabolite gene clusters. *Front. Microbiol.* 6, 299.

(4) Kong, Q., Chi, C., Yu, J., Shan, S., Li, Q., Li, Q., Guan, B., Nierman, W. C., and Bennett, J. W. (2014) The inhibitory effect of *Bacillus megaterium* on aflatoxin and cyclopiazonic acid biosynthetic pathway gene expression in *Aspergillus flavus. Appl Microbiol. Biotechnol.* 98, 5161-5172.

(5) Hayward, A. C. (1991) Biology and epidemiology of bacterial wilt caused by pseudomonas solanacearum. *Annu. Rev. Phytopathol.* 29, 65-87.

(6) Spraker, J. E., Sanchez, L. M., Lowe, T. M., Dorrestein, P. C., and Keller, N. P. (2016) *Ralstonia solanacearum* lipopeptide induces chlamydospore development in fungi and facilitates bacterial entry into fungal tissues. *ISME J* 10, 2317-2330.

(7) Murai, Y., Mori, S., Konno, H., Hikichi, Y., and Kai, K. (2017) Ralstonins A and B, Lipopeptides with Chlamydospore-Inducing and Phytotoxic Activities from the Plant Pathogen *Ralstonia solanacearum. Org. Lett.* 19, 4175-4178

(8) Khaldi, N., Seifuddin, F. T., Turner, G., and Haft, D. (2010) SMURF: Genomic mapping of fungal secondary metabolite clusters. *Fungal Genet. Biol.* 47, 736-741.

(9) Imamura, K., Tsuyama, Y., Hirata, T., Shiraishi, S., Sakamoto, K., Yamada, O., Akita, O., and Shimoi, H. (2012) Identification of a Gene Involved in the Synthesis of a Dipeptidyl Peptidase IV Inhibitor in *Aspergillus oryzae. Appl. Environ. Microbiol.* 78, 6996-7002.

(10) Imamura, K., Tsuyama, Y., and Hirata, T. (2011) Identification and characterization of a novel fermented substance produced by edible *Aspergillus oryzae* AO-1 that inhibits DPP-IV activity. *J. Biosci. Bioeng.* 111, 37-40.

(11) Baccile, J. A., Spraker, J. E., and Le, H. H. (2016) Plant-like biosynthesis of isoquinoline alkaloids in *Aspergillus fumigatus. Nat. Chem. Biol.* 12,419-424.

(12) Porquier, A., Morgant, G., Moraga, J., Dalmais, B., Luyten, I., Simon, A., Pradier, J.-M., Amselem, J., Collado, I. G., and Viaud, M. (2016) The botrydial biosynthetic gene cluster of *Botrytis cinerea* displays a bipartite genomic structure and is positively regulated by the putative Zn(II) 2Cys6 transcription factor BcBot6. *Fungal Genet. Biol.* 96, 33-46.

(13) Asai, Y., Nonaka, N., Nishio, M., Okamura, K., and Date, T. (1997) TMC-2A,-2B and-2C, new dipeptidyl peptidase IV inhibitors produced by *Aspergillus oryzae* A374. II. Isolation and structure determination. *J. Antibiot.* 50, 653-658.

(14) Walsh, C. T. (2008) The chemical versatility of natural-product assembly lines. *Acc. Chem. Res.* 41, 4-10.

(15) Fischer, G. J., Bacon, W., Yang, J., Palmer, J. M., Dagenais, T., Hammock, B. D., and Keller, N. P. (2017) Lipoxygenase Activity Accelerates Programmed Spore Germination in *Aspergillus fumigatus. Front. Microbiol.* 8, 831.

(16) Ayerst, G. (1969) The effects of moisture and temperature on growth and spore germination in some fungi. *J. Stored Prod. Res.* 5, 127-141.

(17) Averyanov, A. A., Lapikova, V. P., and Pasechnik, T. D. (2007) Suppression of early stages of fungus development by hydrogen peroxide at low concentrations. *Plant Pathol. J.* 6, 242-247.

(18) Dong, S. F., Yasui, N., Negishb, H., and Kishimoto, A. (2015) Increased Oxidative Stress in Cultured 3T3-L1 Cells was Attenuated by Berberine Treatment. *Nat. Prod. Commun.* 10, 895-897.

(19) Baskaran, R., Poornima, P., Huang, C. Y., and Padma, V. V. (2016) Neferine prevents NF-κB translocation and protects muscle cells from oxidative stress and apoptosis induced by hypoxia. *Biofactors* 42, 407-417.

(20) Choi, Y. H. (2016) Berberine Hydrochloride Protects C2C12 Myoblast Cells Against Oxidative Stress-Induced Damage via Induction of Nrf-2-Mediated HO-1 Expression. *Drug Dev. Res.* 77, 310-318.

(21) Zheng, H., Kim, J., Liew, M., Yan, J. K., Herrera, O., Bok, J. W., Kelleher, N. L., Keller, N. P., and Wang, Y. (2015) Redox metabolites signal polymicrobial biofilm development via the NapA oxidative stress cascade in *Aspergillus. Curr. Biol.* 25, 29-37.

(22) Chi, M.-H., and Craven, K. D. (2016) RacA-Mediated ROS Signaling Is Required for Polarized Cell Differentiation in Conidiogenesis of *Aspergillus fumigatus. PLoS ONE* 11, e0149548.

(23) Zhao, W., Wisniewski, M., Wang, W., Liu, J., and Liu, Y. (2014) Heat-induced oxidative injury contributes to inhibition of *Botrytis cinerea* spore germination and growth. *World J. Microbiol. Biotechnol.* 30, 951-957.

(24) Averyanov, A. A., and Lapikova, V. P. (1990) ACTIVATED OXYGEN AS A POSSIBLE FACTOR IN THE AUTOINHIBITION OF SPORE GERMINATION OF THE FUNGUS PYRICULARIA-ORYZAE. *Biochemistry-Moscow* 55, 1397-1402.

(25) Averyanov, A. A., Lapikova, V. P., and Pasechnik, T. D. (2011) Self-inhibition of spore germination via reactive oxygen in the fungus Cladosporium cucumerinum, causal agent of cucurbit scab. *Eur. J. Plant Pathol.* 130, 541-550.

(26) Oh, Y. T., Ahn, C. S., Kim, J. G., Ro, H. S., and Lee, C. W. (2010) Proteomic analysis of early phase of conidia germination in *Aspergillusnidulans. Fungal Genet. Biol.* 47, 246-253.

(27) Yao, S. H., Guo, Y., Wang, Y. Z., Zhang, D., and Xu, L. (2016) A cytoplasmic Cu—Zn superoxide dismutase SOD1 contributes to hyphal growth and virulence of *Fusarium graminearum. Fungal Genet. Biol.* 91, 32-42.

(28) Sato, I., Shimizu, M., Hoshino, T., and Takaya, N. (2009) The glutathione system of *Aspergillus nidulans* involves a fungus-specific glutathione S-transferase. *J. Biol. Chem.* 284, 8042-8053.

(29) Liu, C., Sheng, J., Chen, L., Zheng, Y., Lee, D. Y. W., Yang, Y., Xu, M., and Shen, L. (2015) Biocontrol Activity of *Bacillus subtilis* Isolated from Agaricus bisporus Mushroom Compost Against Pathogenic Fungi. *J. Agric. Food Chem.* 63, 6009-6018.

(30) Olmedo, G. M., Cerioni, L., González, M. M., Cabrerizo, F. M., Rapisarda, V. A., and Volentini, S. I. (2017) Antifungal activity of β-carbolines on *Penicillium digitatum* and *Botrytis cinerea. Food Microbiol.* 62, 9-14.

(31) Arrebola, E., Jacobs, R., and Korsten, L. (2010) Iturin A is the principal inhibitor in the biocontrol activity of *Bacillus amyloliquefaciens* PPCB004 against postharvest fungal pathogens. *J. Appl. Microbiol.* 108, 386-395.

(32) Shimizu, K., and Keller, N. P. (2001) Genetic involvement of a cAMP-dependent protein kinase in a G protein signaling pathway regulating morphological and chemical transitions in *Aspergillus nidulans. Genetics* 157, 591-600.

(33) Miyamoto, K., Murakami, T., Kakumyan, P., Keller, N. P., and Matsui, K. (2014) Formation of 1-octen-3-ol from *Aspergillus flavus* conidia is accelerated after disruption of cells independently of Ppo oxygenases, and is not a main cause of inhibition of germination. *PeerJ* 2, e395.

(34) Bok, J. W., Wiemann, P., Garvey, G. S., Lim, F. Y., Haas, B., Wortman, J., and Keller, N. P. (2014) 1llumina identification of RsrA, a conserved C2H2 transcription factor coordinating the NapA mediated oxidative stress signaling pathway in *Aspergillus. BMC Genomics* 15, 1011.

(35) Qin, S., Xing, K., Jiang, J.-H., Xu, L.-H., and Li, W.-J. (2011) Biodiversity, bioactive natural products and biotechnological potential of plant-associated endophytic actinobacteria. *Appi. Microbiol. Biotechnol.* 89, 457-473.

What is claimed is:

1. A method of promoting fungal spore germination, the method comprising contacting a fungal spore with a germination-promoting concentration of an exogenous imizoquin, wherein the exogenous imizoquin has a structure as shown in Formula (I):

(I)

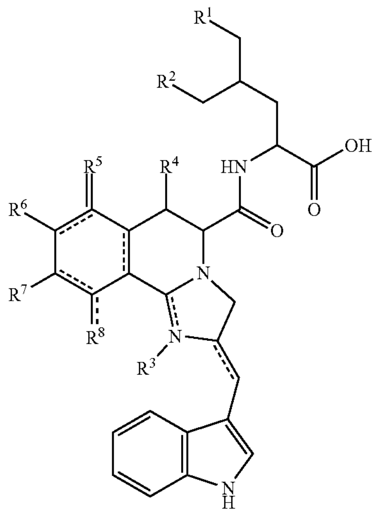

wherein $R^1$, $R^2$, $R^4$, and $R^6$ are independently selected from hydrogen or hydroxyl (—OH);

$R^3$ is hydrogen or is absent;

$R^5$ and $R^8$ are independently selected from hydrogen, hydroxyl, or oxo (═O); and $R^7$ is $C_1$-$C_6$-alkoxy;

and salts thereof.

2. The method of claim 1, wherein at least one of $R^1$, $R^2$, $R^4$, or $R^6$ is hydroxyl.

3. The method of claim 1, wherein at least two of $R^1$, $R^2$, $R^4$, or $R^6$ are hydroxyl.

4. The method of claim 1, wherein at least three of $R^1$, $R^2$, $R^4$, or $R^6$ are hydroxyl.

5. The method of claim 1, wherein $R^1$, $R^2$, $R^4$, and $R^6$ are hydroxyl.

6. The method of claim 1, wherein $R^3$ is hydrogen.

7. The method of claim 1, wherein $R^3$ is absent.

8. The method of claim 1, wherein one of $R^5$ or $R^8$ is hydroxyl.

9. The method of claim 1, wherein one of $R^5$ or $R^8$ is oxo.

10. The method of claim 1, wherein $R^5$ and $R^8$ are independently selected from hydroxyl or oxo.

11. The method of claim 1, wherein $R^7$ is $C_1$-$C_3$-alkoxy.

12. The method of claim 1, wherein $R^7$ is methoxy.

13. The method of claim 1, wherein:

$R^1$, $R^2$, and $R^6$ are independently selected from hydrogen or hydroxyl;

$R^4$ is hydrogen;

$R^3$ is hydrogen or is absent;

$R^5$ and $R^8$ are oxo (═O); and $R^7$ is $C_1$-$C_6$-alkoxy.

14. The method of claim 13, wherein $R^3$ is hydrogen.

15. The method of claim 13, wherein $R^3$ is absent.

16. The method of claim 1, wherein:

$R^1$, $R^2$, and $R^6$ are independently selected from hydrogen or hydroxyl (—OH);

$R^4$ is hydrogen;

$R^3$ is hydrogen or is absent;

$R^5$ and $R^8$ are hydroxy; and $R^7$ is $C_1$-$C_6$-alkoxy.

17. The method of claim 16, wherein $R^3$ is hydrogen.

18. The method of claim 16, wherein $R^3$ is absent.

19. The method of claim 1, wherein:

$R^1$, $R^2$, and $R^6$ are independently selected from hydrogen or hydroxyl (—OH);

$R^4$ is hydrogen;

$R^3$ is hydrogen or is absent;

$R^5$ and $R^8$ are oxo (═O); and $R^7$ is methoxy.

20. The method of claim 19, wherein $R^3$ is hydrogen.

21. The method of claim 19, wherein $R^3$ is absent.

22. The method of claim 1, wherein:

$R^1$, $R^2$, and $R^6$ are independently selected from hydrogen or hydroxyl (—OH);

$R^4$ is hydrogen;

$R^3$ is hydrogen or is absent;

$R^5$ and $R^8$ are hydroxy; and $R^7$ is methoxy;

and salts thereof.

23. The method of claim 22, wherein $R^3$ is hydrogen.

24. The method of claim 22, wherein $R^3$ is absent.

25. The method of claim 1, wherein the concentration of the exogenous imizoquin is from 0.1 mM to 0.4 mM.

* * * * *